United States Patent
Blain

(10) Patent No.: US 9,808,294 B2
(45) Date of Patent: Nov. 7, 2017

(54) METHODS AND APPARATUS FOR STABILIZING BONE

(71) Applicant: Spinal Elements, Inc., Carlsbad, CA (US)

(72) Inventor: Jason Blain, Encinitas, CA (US)

(73) Assignee: Spinal Elements, Inc., Carlsbad, CA (US)

(*) Notice: Subject to any disclaimer, the term of this patent is extended or adjusted under 35 U.S.C. 154(b) by 35 days.

(21) Appl. No.: 14/869,793

(22) Filed: Sep. 29, 2015

(65) Prior Publication Data

US 2016/0051294 A1 Feb. 25, 2016

Related U.S. Application Data

(60) Continuation of application No. 14/256,532, filed on Apr. 18, 2014, now Pat. No. 9,179,943, which is a
(Continued)

(51) Int. Cl.
| | |
|---|---|
| *A61B 17/70* | (2006.01) |
| *A61B 17/84* | (2006.01) |
| *A61B 17/82* | (2006.01) |

(52) U.S. Cl.
CPC ......... *A61B 17/7064* (2013.01); *A61B 17/82* (2013.01); *A61B 17/842* (2013.01); *A61B 17/7053* (2013.01)

(58) Field of Classification Search
CPC ... A61B 17/7064; A61B 17/842; A61B 17/82; A61B 17/7053

USPC ......... 606/246–249, 74, 263, 279, 151, 213, 606/215, 216, 228; 623/13.11–13.14, 623/17.11, 17.15; 24/16 R, 17 AP
See application file for complete search history.

(56) References Cited

U.S. PATENT DOCUMENTS

| | | |
|---|---|---|
| 86,016 A | 1/1869 | Howell |
| 1,630,239 A | 5/1927 | Binkley et al. |

(Continued)

FOREIGN PATENT DOCUMENTS

| | | |
|---|---|---|
| CA | 2 437 575 | 4/2009 |
| DE | 93 04 368 | 5/1993 |

(Continued)

OTHER PUBLICATIONS

3rd Party Lab Notebook, "Facet Cartilage Repair," dated May 20, 2003 in 2 pages.
(Continued)

*Primary Examiner* — Pedro Philogene
*Assistant Examiner* — David C Comstock
(74) *Attorney, Agent, or Firm* — Knobbe, Martens, Olson & Bear, LLP

(57) ABSTRACT

In some embodiments, a method comprises disposing a portion of a flexible fastening band into contact with a first bone portion and into contact with a second bone portion. The portion of the flexible fastening band having a substantially uniform shape configured to substantially compliment a shape of the first bone portion and a shape of the second bone portion. The method further includes inserting the portion of the flexible fastening band into a fastener and advancing the portion of the flexible fastening band through the fastener until the first bone portion and the and the second bone portion are stabilized.

21 Claims, 26 Drawing Sheets

Related U.S. Application Data division of application No. 13/033,791, filed on Feb. 24, 2011, now Pat. No. 8,740,949.

(56) References Cited

U.S. PATENT DOCUMENTS

| | | |
|---|---|---|
| 1,822,280 A | 9/1931 | Ervay |
| 1,822,330 A | 9/1931 | Anslie |
| 2,486,303 A | 10/1949 | Longfellow |
| 2,706,023 A | 4/1955 | Merritt |
| 3,111,945 A | 11/1963 | Von Solbrig |
| 3,149,808 A | 9/1964 | Weckesser |
| 3,570,497 A | 3/1971 | Lemole |
| 3,867,728 A | 2/1975 | Stubstad et al. |
| 3,875,595 A | 4/1975 | Froning |
| 3,879,767 A | 4/1975 | Stubstad |
| 4,001,896 A | 1/1977 | Arkangel |
| 4,037,603 A | 7/1977 | Wendorff |
| 4,085,466 A | 4/1978 | Goodfellow et al. |
| 4,119,091 A | 10/1978 | Partridge |
| 4,156,296 A | 5/1979 | Johnson et al. |
| 4,231,121 A | 11/1980 | Lewis |
| D261,935 S | 11/1981 | Halloran |
| 4,312,337 A | 1/1982 | Donohue |
| 4,323,217 A | 4/1982 | Dochterman |
| 4,349,921 A | 9/1982 | Kuntz |
| 4,502,161 A | 3/1985 | Wall |
| D279,502 S | 7/1985 | Halloran |
| D279,503 S | 7/1985 | Halloran |
| 4,535,764 A | 8/1985 | Ebert |
| 4,573,458 A | 3/1986 | Lower |
| 4,573,459 A | 3/1986 | Litton |
| 4,634,445 A | 1/1987 | Helal |
| 4,662,371 A | 5/1987 | Whipple et al. |
| 4,706,659 A | 11/1987 | Matthews et al. |
| 4,714,469 A | 12/1987 | Kenna |
| 4,722,331 A | 2/1988 | Fox |
| 4,730,615 A | 3/1988 | Sutherland et al. |
| 4,759,766 A | 7/1988 | Buettner-Janz et al. |
| 4,759,769 A | 7/1988 | Hedman et al. |
| 4,772,287 A | 9/1988 | Ray et al. |
| 4,773,402 A | 9/1988 | Asher et al. |
| 4,834,757 A | 5/1989 | Brantigan |
| 4,863,477 A | 9/1989 | Monson |
| 4,904,260 A | 2/1990 | Ray et al. |
| 4,907,577 A | 3/1990 | Wu |
| 4,911,718 A | 3/1990 | Lee et al. |
| 4,919,667 A | 4/1990 | Richmond |
| 4,923,471 A | 5/1990 | Morgan |
| 4,936,848 A | 6/1990 | Bagby |
| 4,941,466 A | 7/1990 | Romano |
| 4,959,065 A | 9/1990 | Arnett et al. |
| 4,969,909 A | 11/1990 | Barouk |
| 5,000,165 A | 3/1991 | Watanabe |
| 5,002,546 A | 3/1991 | Romano |
| 5,011,484 A | 4/1991 | Bréard |
| 5,015,255 A | 5/1991 | Kuslich |
| 5,047,055 A | 9/1991 | Bao et al. |
| 5,062,845 A | 11/1991 | Kuslich |
| 5,071,437 A | 12/1991 | Steffee |
| 5,092,866 A | 3/1992 | Breard et al. |
| 5,112,013 A | 5/1992 | Tolbert et al. |
| 5,112,346 A | 5/1992 | Hiltebrandt et al. |
| 5,127,912 A | 7/1992 | Ray et al. |
| 5,135,188 A | 8/1992 | Anderson et al. |
| 5,147,404 A | 9/1992 | Downey |
| 5,171,280 A | 12/1992 | Baumgartner |
| 5,192,326 A | 3/1993 | Bao et al. |
| 5,209,755 A | 5/1993 | Abrahan et al. |
| 5,258,031 A | 11/1993 | Salib et al. |
| 5,282,861 A | 2/1994 | Kaplan |
| 5,286,249 A | 2/1994 | Thibodaux |
| 5,300,073 A | 4/1994 | Ray et al. |
| 5,306,275 A | 4/1994 | Bryan |
| 5,306,308 A | 4/1994 | Gross et al. |
| 5,306,309 A | 4/1994 | Wagner et al. |
| 5,330,479 A | 7/1994 | Whitmore |
| 5,360,431 A | 11/1994 | Puno et al. |
| 5,368,596 A | 11/1994 | Brookhart |
| 5,370,697 A | 12/1994 | Baumgartner |
| 5,372,598 A | 12/1994 | Luhr et al. |
| 5,400,784 A | 3/1995 | Durand et al. |
| 5,401,269 A | 3/1995 | Buttner-Janz et al. |
| 5,413,576 A | 5/1995 | Rivard |
| 5,415,661 A | 5/1995 | Holmes |
| 5,425,773 A | 6/1995 | Boyd et al. |
| 5,437,672 A | 8/1995 | Alleyne |
| 5,445,639 A | 8/1995 | Kuslich et al. |
| 5,458,642 A | 10/1995 | Beer et al. |
| 5,458,643 A | 10/1995 | Oka et al. |
| 5,462,542 A | 10/1995 | Alesi, Jr. |
| 5,487,756 A | 1/1996 | Kallesoe et al. |
| 5,491,882 A | 2/1996 | Walston et al. |
| 5,496,318 A | 3/1996 | Howland et al. |
| 5,507,823 A | 4/1996 | Walston et al. |
| 5,509,918 A | 4/1996 | Romano |
| 5,514,180 A | 5/1996 | Heggeness et al. |
| 5,527,312 A | 6/1996 | Ray |
| 5,527,314 A | 6/1996 | Brumfield et al. |
| 5,534,028 A | 7/1996 | Bao et al. |
| 5,534,030 A | 7/1996 | Navarro et al. |
| 5,540,706 A | 7/1996 | Aust et al. |
| 5,545,229 A | 8/1996 | Parsons et al. |
| 5,549,619 A | 8/1996 | Peters et al. |
| 5,556,431 A | 9/1996 | Buttner-Janz |
| 5,562,738 A | 10/1996 | Boyd et al. |
| 5,571,105 A | 11/1996 | Gundolf |
| 5,571,131 A | 11/1996 | Ek et al. |
| 5,571,189 A | 11/1996 | Kuslich |
| 5,571,191 A | 11/1996 | Fitz |
| 5,577,995 A | 11/1996 | Walker et al. |
| 5,586,989 A | 12/1996 | Bray, Jr. |
| 5,591,165 A | 1/1997 | Jackson |
| 5,603,713 A | 2/1997 | Aust et al. |
| 5,638,700 A | 6/1997 | Shechter |
| 5,645,597 A | 7/1997 | Krapiva |
| 5,645,599 A | 7/1997 | Samani |
| 5,649,947 A | 7/1997 | Auerbach et al. |
| 5,653,762 A | 8/1997 | Pisharodi |
| 5,674,295 A | 10/1997 | Ray et al. |
| 5,674,296 A | 10/1997 | Bryan et al. |
| 5,676,701 A | 10/1997 | Yuan et al. |
| 5,683,464 A | 11/1997 | Wagner et al. |
| 5,683,466 A | 11/1997 | Vitale |
| 5,700,265 A | 12/1997 | Romano |
| 5,702,450 A | 12/1997 | Bisserie |
| 5,707,373 A | 1/1998 | Sevrain et al. |
| 5,713,542 A | 2/1998 | Benoit |
| 5,716,415 A | 2/1998 | Steffee |
| 5,725,582 A | 3/1998 | Bevan et al. |
| 5,741,260 A | 4/1998 | Songer et al. |
| 5,741,261 A | 4/1998 | Moskovitz et al. |
| D395,138 S | 6/1998 | Ohata |
| 5,766,251 A | 6/1998 | Koshino |
| 5,766,253 A | 6/1998 | Brosnahan |
| 5,772,663 A | 6/1998 | Whiteside et al. |
| 5,797,916 A | 8/1998 | McDowell |
| 5,824,093 A | 10/1998 | Ray et al. |
| 5,824,094 A | 10/1998 | Serhan et al. |
| 5,836,948 A | 11/1998 | Zucherman et al. |
| 5,851,208 A | 12/1998 | Trott |
| 5,860,977 A | 1/1999 | Zucherman et al. |
| 5,865,846 A | 2/1999 | Bryan et al. |
| 5,868,745 A | 2/1999 | Alleyne |
| 5,876,404 A | 3/1999 | Zucherman et al. |
| 5,879,396 A | 3/1999 | Walston et al. |
| 5,888,203 A | 3/1999 | Goldberg |
| 5,893,889 A | 4/1999 | Harrington |
| 5,895,428 A | 4/1999 | Berry |
| RE36,221 E | 6/1999 | Breard et al. |
| 5,918,604 A | 7/1999 | Whelan |
| 5,951,555 A | 9/1999 | Rehak et al. |
| 5,964,765 A | 10/1999 | Fenton et al. |
| 5,993,452 A | 11/1999 | Vandewalle |
| 5,997,542 A | 12/1999 | Burke |

(56) References Cited

U.S. PATENT DOCUMENTS

| | | |
|---|---|---|
| 6,001,130 A | 12/1999 | Bryan et al. |
| 6,014,588 A | 1/2000 | Fitz |
| 6,019,763 A | 2/2000 | Nakamura et al. |
| 6,019,792 A | 2/2000 | Cauthen |
| 6,039,763 A | 3/2000 | Shelokov |
| 6,048,342 A | 4/2000 | Zucherman et al. |
| 6,050,998 A | 4/2000 | Fletcher |
| 6,063,121 A | 5/2000 | Xavier et al. |
| 6,066,325 A | 5/2000 | Wallace et al. |
| 6,068,630 A | 5/2000 | Zucherman et al. |
| RE36,758 E | 6/2000 | Fitz |
| 6,080,157 A | 6/2000 | Cathro et al. |
| 6,099,531 A | 8/2000 | Bonutti |
| 6,102,347 A | 8/2000 | Benoit |
| 6,106,558 A | 8/2000 | Picha |
| 6,113,637 A | 9/2000 | Gill et al. |
| 6,132,464 A | 10/2000 | Martin |
| 6,132,465 A | 10/2000 | Ray et al. |
| 6,146,422 A | 11/2000 | Lawson |
| 6,156,067 A | 12/2000 | Bryan et al. |
| 6,179,839 B1 | 1/2001 | Weiss et al. |
| D439,340 S | 3/2001 | Michelson |
| 6,200,322 B1 | 3/2001 | Branch et al. |
| 6,293,949 B1 | 9/2001 | Justis et al. |
| D450,122 S | 11/2001 | Michelson |
| 6,325,803 B1 | 12/2001 | Schumacher et al. |
| D454,953 S | 3/2002 | Michelson |
| 6,368,325 B1 | 4/2002 | McKinley et al. |
| 6,368,350 B1 | 4/2002 | Erickson et al. |
| 6,371,958 B1 | 4/2002 | Overaker |
| 6,375,573 B2 | 4/2002 | Romano |
| 6,379,386 B1 | 4/2002 | Resch et al. |
| D460,188 S | 7/2002 | Michelson |
| D460,189 S | 7/2002 | Michelson |
| 6,419,678 B1 | 7/2002 | Asfora |
| 6,419,703 B1 | 7/2002 | Fallin et al. |
| 6,436,099 B1 | 8/2002 | Drewry et al. |
| 6,436,101 B1 | 8/2002 | Hamada |
| 6,436,146 B1 | 8/2002 | Hassler et al. |
| D463,560 S | 9/2002 | Michelson |
| 6,470,207 B1 | 10/2002 | Simon et al. |
| 6,565,605 B2 | 5/2003 | Goble et al. |
| 6,572,617 B1 | 6/2003 | Senegas |
| 6,579,318 B2 | 6/2003 | Varga et al. |
| 6,579,319 B2 | 6/2003 | Goble et al. |
| 6,589,244 B1 | 7/2003 | Sevrain et al. |
| 6,600,956 B2 | 7/2003 | Maschino et al. |
| 6,607,530 B1 | 8/2003 | Carl et al. |
| 6,610,091 B1 | 8/2003 | Reiley |
| D479,331 S | 9/2003 | Pike et al. |
| 6,626,944 B1 | 9/2003 | Taylor |
| 6,641,614 B1 | 11/2003 | Wagner et al. |
| 6,656,195 B2 | 12/2003 | Peters et al. |
| 6,669,697 B1 | 12/2003 | Pisharodi |
| 6,669,729 B2 | 12/2003 | Chin |
| 6,706,068 B2 | 3/2004 | Ferree |
| 6,743,232 B2 | 6/2004 | Overaker et al. |
| 6,761,720 B1 | 7/2004 | Senegas |
| 6,764,491 B2 | 7/2004 | Frey et al. |
| 6,770,095 B2 | 8/2004 | Grinberg et al. |
| 6,783,527 B2 | 8/2004 | Drewry et al. |
| 6,790,210 B1 | 9/2004 | Cragg et al. |
| 6,802,863 B2 | 10/2004 | Lawson et al. |
| 6,811,567 B2 | 11/2004 | Reiley |
| 6,902,566 B2 | 6/2005 | Zucherman et al. |
| 6,908,484 B2 | 6/2005 | Zubok et al. |
| 6,966,930 B2 | 11/2005 | Arnin et al. |
| 6,974,478 B2 | 12/2005 | Reiley et al. |
| 6,974,479 B2 | 12/2005 | Trieu |
| D517,404 S | 3/2006 | Schluter |
| 7,008,429 B2 | 3/2006 | Golobek |
| 7,013,675 B2 | 3/2006 | Marquez-Pickering |
| 7,051,451 B2 | 5/2006 | Augostino et al. |
| 7,074,238 B2 | 7/2006 | Stinson et al. |
| 7,101,375 B2 | 9/2006 | Zucherman et al. |
| 7,223,269 B2 | 5/2007 | Chappuis |
| D565,180 S | 3/2008 | Liao |
| 7,371,238 B2 | 5/2008 | Sololeski et al. |
| 7,458,981 B2 | 12/2008 | Fielding et al. |
| 7,517,358 B2 | 4/2009 | Petersen |
| 7,537,611 B2 | 5/2009 | Lee |
| 7,559,940 B2 | 7/2009 | McGuire et al. |
| 7,563,286 B2 | 7/2009 | Gerber et al. |
| 7,585,300 B2 | 9/2009 | Cha |
| 7,608,104 B2 | 10/2009 | Yuan et al. |
| 7,695,472 B2 | 4/2010 | Young |
| 7,799,077 B2 | 9/2010 | Lang et al. |
| 7,806,895 B2 | 10/2010 | Weier et al. |
| 7,846,183 B2 | 12/2010 | Blain |
| 7,862,590 B2 | 1/2011 | Lim et al. |
| 7,935,136 B2 | 5/2011 | Alamin et al. |
| D643,121 S | 8/2011 | Milford et al. |
| 7,993,370 B2 | 8/2011 | Jahng |
| 7,998,172 B2 | 8/2011 | Blain |
| 8,052,728 B2 | 11/2011 | Hestad |
| 8,109,971 B2 | 2/2012 | Hale |
| 8,133,225 B2 | 3/2012 | Pieske |
| 8,163,016 B2 | 4/2012 | Linares |
| 8,192,468 B2 | 6/2012 | Biedermann et al. |
| 8,216,275 B2 | 7/2012 | Fielding et al. |
| 8,246,655 B2 | 8/2012 | Jackson et al. |
| 8,292,954 B2 | 10/2012 | Robinson et al. |
| 8,306,307 B2 | 11/2012 | Koike et al. |
| 8,394,125 B2 | 3/2013 | Assell |
| 8,460,346 B2 | 6/2013 | Ralph et al. |
| 8,486,078 B2 | 7/2013 | Carl et al. |
| 8,496,691 B2 | 7/2013 | Blain |
| 8,579,903 B2 | 11/2013 | Carl |
| 8,652,137 B2 | 2/2014 | Blain et al. |
| 8,740,942 B2 | 6/2014 | Blain |
| 8,740,949 B2 | 6/2014 | Blain |
| 8,784,423 B2 | 7/2014 | Kowarsch et al. |
| 8,858,597 B2 | 10/2014 | Blain |
| 8,882,804 B2 | 11/2014 | Blain |
| 8,961,613 B2 | 2/2015 | Assell et al. |
| D724,733 S | 3/2015 | Blain et al. |
| 8,974,456 B2 | 3/2015 | Allen et al. |
| 8,979,529 B2 | 3/2015 | Marcus |
| 8,992,533 B2 | 3/2015 | Blain et al. |
| 8,998,953 B2 | 4/2015 | Blain |
| 9,017,389 B2 | 4/2015 | Assell et al. |
| 9,060,787 B2 | 6/2015 | Blain et al. |
| D739,935 S | 9/2015 | Blain et al. |
| 9,149,283 B2 | 10/2015 | Assell et al. |
| 9,161,763 B2 | 10/2015 | Assell et al. |
| 9,179,943 B2 * | 11/2015 | Blain ................ A61B 17/7064 |
| 9,220,547 B2 | 12/2015 | Blain et al. |
| D748,262 S | 1/2016 | Blain |
| 9,233,006 B2 | 1/2016 | Assell et al. |
| D748,793 S | 2/2016 | Blain |
| 9,265,546 B2 | 2/2016 | Blain |
| 9,271,765 B2 | 3/2016 | Blain |
| 9,301,786 B2 | 4/2016 | Blain |
| 9,314,277 B2 | 4/2016 | Assell et al. |
| 9,345,488 B2 | 5/2016 | Assell et al. |
| 9,421,044 B2 | 8/2016 | Blain et al. |
| D765,853 S | 9/2016 | Blain et al. |
| D765,854 S | 9/2016 | Blain et al. |
| 9,456,855 B2 | 10/2016 | Blain et al. |
| 9,517,077 B2 | 12/2016 | Blain et al. |
| D777,921 S | 1/2017 | Blain et al. |
| D780,315 S | 2/2017 | Blain et al. |
| 9,572,602 B2 | 2/2017 | Blain et al. |
| 2001/0018614 A1 | 8/2001 | Bianchi |
| 2002/0018799 A1 | 2/2002 | Spector et al. |
| 2002/0019637 A1 | 2/2002 | Frey et al. |
| 2002/0029039 A1 | 3/2002 | Zucherman et al. |
| 2002/0040227 A1 | 4/2002 | Harari |
| 2002/0065557 A1 | 5/2002 | Goble et al. |
| 2002/0072800 A1 | 6/2002 | Goble et al. |
| 2002/0077700 A1 | 6/2002 | Varga et al. |
| 2002/0086047 A1 | 7/2002 | Mueller et al. |
| 2002/0120335 A1 | 8/2002 | Angelucci et al. |
| 2002/0123806 A1 | 9/2002 | Reiley |

(56) References Cited

U.S. PATENT DOCUMENTS

| | | |
|---|---|---|
| 2002/0151895 A1 | 10/2002 | Soboleski et al. |
| 2002/0173800 A1 | 11/2002 | Dreyfuss et al. |
| 2002/0173813 A1 | 11/2002 | Peterson et al. |
| 2002/0198527 A1 | 12/2002 | Muckter |
| 2003/0004572 A1 | 1/2003 | Goble et al. |
| 2003/0028250 A1 | 2/2003 | Reiley et al. |
| 2003/0040797 A1 | 2/2003 | Fallin et al. |
| 2003/0120343 A1 | 6/2003 | Whelan |
| 2003/0176919 A1 | 9/2003 | Schmieding |
| 2003/0176922 A1 | 9/2003 | Lawson et al. |
| 2003/0187454 A1 | 10/2003 | Gill et al. |
| 2003/0191532 A1 | 10/2003 | Goble et al. |
| 2003/0204259 A1 | 10/2003 | Goble et al. |
| 2003/0216669 A1 | 11/2003 | Lang et al. |
| 2003/0233146 A1 | 12/2003 | Grinberg et al. |
| 2004/0006391 A1 | 1/2004 | Reiley |
| 2004/0010318 A1 | 1/2004 | Ferree |
| 2004/0024462 A1 | 2/2004 | Ferree et al. |
| 2004/0049271 A1 | 3/2004 | Biedermann et al. |
| 2004/0049272 A1 | 3/2004 | Reiley |
| 2004/0049273 A1 | 3/2004 | Reiley |
| 2004/0049274 A1 | 3/2004 | Reiley |
| 2004/0049275 A1 | 3/2004 | Reiley |
| 2004/0049276 A1 | 3/2004 | Reiley |
| 2004/0049277 A1 | 3/2004 | Reiley |
| 2004/0049278 A1 | 3/2004 | Reiley |
| 2004/0049281 A1 | 3/2004 | Reiley |
| 2004/0059429 A1 | 3/2004 | Amin et al. |
| 2004/0087954 A1 | 5/2004 | Allen et al. |
| 2004/0116927 A1 | 6/2004 | Graf |
| 2004/0127989 A1 | 7/2004 | Dooris et al. |
| 2004/0143264 A1 | 7/2004 | McAfee |
| 2004/0176844 A1 | 9/2004 | Zubok et al. |
| 2004/0199166 A1 | 10/2004 | Schmieding et al. |
| 2004/0215341 A1 | 10/2004 | Sybert et al. |
| 2004/0230201 A1 | 11/2004 | Yuan et al. |
| 2004/0230304 A1 | 11/2004 | Yuan et al. |
| 2005/0010291 A1 | 1/2005 | Stinson et al. |
| 2005/0015146 A1 | 1/2005 | Louis et al. |
| 2005/0043797 A1 | 2/2005 | Lee |
| 2005/0043799 A1 | 2/2005 | Reiley |
| 2005/0049705 A1 | 3/2005 | Hale et al. |
| 2005/0055096 A1 | 3/2005 | Serhan et al. |
| 2005/0059972 A1 | 3/2005 | Biscup |
| 2005/0131409 A1 | 6/2005 | Chervitz et al. |
| 2005/0131538 A1 | 6/2005 | Chervitz et al. |
| 2005/0143818 A1 | 6/2005 | Yuan et al. |
| 2005/0159746 A1 | 7/2005 | Grab et al. |
| 2005/0197700 A1 | 9/2005 | Boehem et al. |
| 2005/0216017 A1 | 9/2005 | Fielding et al. |
| 2005/0240201 A1 | 10/2005 | Yeung |
| 2005/0251256 A1 | 11/2005 | Reiley |
| 2005/0256494 A1 | 11/2005 | Datta |
| 2006/0004367 A1 | 1/2006 | Alamin et al. |
| 2006/0036323 A1 | 2/2006 | Carl et al. |
| 2006/0041311 A1 | 2/2006 | McLeer |
| 2006/0084985 A1 | 4/2006 | Kim |
| 2006/0085006 A1 | 4/2006 | Ek et al. |
| 2006/0085072 A1 | 4/2006 | Funk et al. |
| 2006/0111782 A1 | 5/2006 | Petersen |
| 2006/0116684 A1 | 6/2006 | Whelan |
| 2006/0149375 A1 | 7/2006 | Yuan et al. |
| 2006/0200137 A1 | 9/2006 | Soboleski et al. |
| 2006/0241601 A1 | 10/2006 | Trautwein et al. |
| 2006/0241758 A1 | 10/2006 | Peterman et al. |
| 2006/0293691 A1 | 12/2006 | Mitra et al. |
| 2007/0055236 A1 | 3/2007 | Hudgins et al. |
| 2007/0055252 A1 | 3/2007 | Blain et al. |
| 2007/0078464 A1 | 4/2007 | Jones et al. |
| 2007/0118218 A1 | 5/2007 | Hooper |
| 2007/0149976 A1 | 6/2007 | Hale et al. |
| 2007/0179619 A1 | 8/2007 | Grab |
| 2007/0250166 A1 | 10/2007 | McKay |
| 2007/0270812 A1 | 11/2007 | Peckham |
| 2008/0009866 A1 | 1/2008 | Alamin et al. |
| 2008/0058929 A1 | 3/2008 | Whelan |
| 2008/0177264 A1 | 7/2008 | Alamin et al. |
| 2008/0183211 A1 | 7/2008 | Lamborne et al. |
| 2008/0228225 A1 | 9/2008 | Trautwein et al. |
| 2008/0287996 A1 | 11/2008 | Soholeski et al. |
| 2009/0005818 A1 | 1/2009 | Chin et al. |
| 2009/0005873 A1 | 1/2009 | Slivka et al. |
| 2009/0018662 A1 | 1/2009 | Pasquet et al. |
| 2009/0024166 A1 | 1/2009 | Carl et al. |
| 2009/0076617 A1 | 3/2009 | Ralph et al. |
| 2009/0125066 A1 | 5/2009 | Kraus et al. |
| 2009/0138048 A1 | 5/2009 | Baccelli et al. |
| 2009/0171360 A1 | 7/2009 | Whelan |
| 2009/0198282 A1 | 8/2009 | Fielding et al. |
| 2009/0264928 A1 | 10/2009 | Blain |
| 2009/0264929 A1 | 10/2009 | Alamin et al. |
| 2009/0270918 A1 | 10/2009 | Attia et al. |
| 2009/0270929 A1 | 10/2009 | Suddaby |
| 2009/0326589 A1 | 12/2009 | Lemoine et al. |
| 2010/0010548 A1 | 1/2010 | Hermida Ochoa |
| 2010/0076503 A1 | 3/2010 | Beyar et al. |
| 2010/0131008 A1 | 5/2010 | Overes et al. |
| 2010/0179553 A1 | 7/2010 | Ralph et al. |
| 2010/0185241 A1 | 7/2010 | Malandain et al. |
| 2010/0191286 A1 | 7/2010 | Butler |
| 2010/0204700 A1 | 8/2010 | Falahee |
| 2010/0204732 A1 | 8/2010 | Alamin et al. |
| 2010/0234894 A1 | 9/2010 | Alamin et al. |
| 2010/0274289 A1 | 10/2010 | Carls et al. |
| 2010/0298829 A1 | 11/2010 | Schaller et al. |
| 2010/0318133 A1 | 12/2010 | Tornier |
| 2011/0022089 A1 | 1/2011 | Assell et al. |
| 2011/0098816 A1 | 4/2011 | Jacob et al. |
| 2011/0160772 A1 | 6/2011 | Arcenio et al. |
| 2011/0172712 A1 | 7/2011 | Chee et al. |
| 2011/0295318 A1 | 12/2011 | Alamin et al. |
| 2012/0035658 A1 | 2/2012 | Goble et al. |
| 2012/0046749 A1 | 2/2012 | Tatsumi |
| 2012/0101502 A1 | 4/2012 | Kartalian et al. |
| 2012/0150231 A1 | 6/2012 | Alamin et al. |
| 2012/0221048 A1 | 8/2012 | Blain |
| 2012/0221049 A1 | 8/2012 | Blain |
| 2012/0221060 A1 | 8/2012 | Blain |
| 2012/0245586 A1 | 9/2012 | Lehenkari et al. |
| 2012/0271354 A1 | 10/2012 | Baccelli et al. |
| 2012/0277801 A1 | 11/2012 | Marik et al. |
| 2013/0023878 A1 | 1/2013 | Belliard et al. |
| 2013/0041410 A1 | 2/2013 | Hestad et al. |
| 2013/0079778 A1 | 3/2013 | Azuero et al. |
| 2013/0123923 A1 | 5/2013 | Pavlov et al. |
| 2013/0325065 A1 | 12/2013 | Malandain et al. |
| 2014/0012318 A1 | 1/2014 | Goel |
| 2014/0066758 A1 | 3/2014 | Marik et al. |
| 2014/0257397 A1 | 9/2014 | Akbarnia et al. |
| 2014/0277142 A1 | 9/2014 | Blain |
| 2014/0277148 A1 | 9/2014 | Blain |
| 2014/0277149 A1 | 9/2014 | Rooney et al. |
| 2014/0336653 A1 | 11/2014 | Bromer |
| 2014/0378976 A1 | 12/2014 | Garcia |
| 2015/0081023 A1 | 3/2015 | Blain |
| 2015/0094766 A1 | 4/2015 | Blain et al. |
| 2015/0094767 A1 | 4/2015 | Blain et al. |
| 2015/0119988 A1 | 4/2015 | Assell et al. |
| 2015/0164516 A1 | 6/2015 | Blain et al. |
| 2015/0164652 A1 | 6/2015 | Assell et al. |
| 2015/0190149 A1 | 7/2015 | Assell et al. |
| 2015/0196330 A1 | 7/2015 | Blain |
| 2015/0209096 A1 | 7/2015 | Gephart |
| 2015/0257770 A1 | 9/2015 | Assell et al. |
| 2015/0257773 A1 | 9/2015 | Blain |
| 2015/0327872 A1 | 11/2015 | Assell et al. |
| 2016/0113692 A1 | 4/2016 | Knoepfle |
| 2016/0128838 A1 | 5/2016 | Assell et al. |
| 2016/0213481 A1 | 7/2016 | Blain |

(56) References Cited

U.S. PATENT DOCUMENTS

| | | | |
|---|---|---|---|
| 2016/0324549 | A1 | 11/2016 | Blain |
| 2017/0000527 | A1 | 1/2017 | Blain et al. |

FOREIGN PATENT DOCUMENTS

| | | |
|---|---|---|
| DE | 201 12 123 | 9/2001 |
| DE | 101 35 771 | 2/2003 |
| EP | 0 238 219 | 9/1987 |
| EP | 0 322 334 | 6/1989 |
| EP | 0 392 124 | 10/1990 |
| EP | 0 610 837 | 8/1994 |
| EP | 0 928 603 | 7/1999 |
| EP | 1 201 202 | 5/2002 |
| EP | 1 201 256 | 5/2002 |
| EP | 2 919 717 | 9/2015 |
| FR | 2 704 745 | 11/1994 |
| FR | 2 722 980 | 2/1996 |
| GB | 2 366 736 | 3/2002 |
| JP | 62-270147 | 11/1987 |
| JP | 10-179622 | 7/1998 |
| JP | 2000-210297 | 8/2000 |
| JP | 2004-508888 | 3/2004 |
| JP | 2004-181236 | 7/2004 |
| JP | 2007-503884 | 3/2007 |
| JP | 2007-517627 | 7/2007 |
| JP | 2007-190389 | 8/2007 |
| JP | 2008-510526 | 4/2008 |
| JP | 2009-533167 | 9/2009 |
| JP | 2013-534451 | 9/2013 |
| MX | 6012309 | 1/2007 |
| WO | WO 93/14721 | 8/1993 |
| WO | WO 94/04088 | 3/1994 |
| WO | WO 97/47246 | 12/1997 |
| WO | WO 98/48717 | 11/1998 |
| WO | WO 99/23963 | 5/1999 |
| WO | WO 00/38582 | 7/2000 |
| WO | WO 00/53126 | 9/2000 |
| WO | WO 01/30248 | 5/2001 |
| WO | WO 02/045765 | 6/2002 |
| WO | WO 02/065954 | 8/2002 |
| WO | WO 02/096300 | 12/2002 |
| WO | WO 03/101350 | 12/2003 |
| WO | WO 2004/071358 | 8/2004 |
| WO | WO 2005/020850 | 3/2005 |
| WO | WO 2005/072661 | 8/2005 |
| WO | WO 2006/023980 | 3/2006 |
| WO | WO 2006/096803 | 9/2006 |
| WO | WO 2009/021876 | 2/2009 |
| WO | WO 2010/060072 | 5/2010 |
| WO | WO 2010/122472 | 10/2010 |
| WO | WO 2011/011621 | 1/2011 |
| WO | WO 2012/007941 | 1/2012 |
| WO | WO 2012/116266 | 8/2012 |
| WO | WO 2013/022880 | 2/2013 |
| WO | WO 2013/138655 | 9/2013 |
| WO | WO 2014/078541 | 5/2014 |
| WO | WO 2016/044432 | 3/2016 |

OTHER PUBLICATIONS

ArthroTek, "CurvTek® Bone Tunneling System," Surgical Technique, 2000, pp. 6.
E-mail from 3rd Party citing U.S. Appl. Nos. 60/721,909; 60/750,005 and 60/749,000, initial e-mail dated May 11, 2009, reply e-mail dated May 18, 2009.
King et al., "Mechanism of Spinal Injury Due to Caudocephalad Acceleration," Symposium on the Lumbar Spine, Orthopedic Clinic of North America, Jan. 1975, vol. 6, pp. 19-31.
Official Communication in Australian Application No. 2005213459, dated Dec. 11, 2009.
Official Communication in Australian Application No. 2005213459, dated Dec. 15, 2010.
Official Communication in Australian Application No. 2011226832, dated Sep. 4, 2012.
Official Communication in Australian Application No. 2011226832, dated Oct. 31, 2012.
Official Communication in Australian Application No. AU2013237744, dated Sep. 2, 2014.
Official Communication in Canadian Application No. 2,555,355, dated Sep. 2, 2011.
Official Communication in European Application No. 05712981.9, dated Jul. 24, 2007.
Official Communication in European Application No. 05712981.9, dated Mar. 10, 2008.
Official Communication in European Application No. 05712981.9, dated Apr. 6, 2009.
Official Communication in European Application No. 05712981.9, dated Jun. 15, 2010.
Official Communication in European Application No. 10178979.0, dated Mar. 14, 2011.
Official Communication in European Application No. 10178979.0, dated Nov. 13, 2012.
Official Communication in European Application No. 10178979.0, dated Aug. 5, 2013.
Official Communication in European Application No. 14175088.5, dated Sep. 8, 2014.
Official Communication in Japanese Application No. 2006-552309, dated May 25, 2010.
Official Communication in Japanese Application No. 2006-552309, dated Feb. 15, 2011.
Official Communication in Japanese Application No. 2010-221380, dated Feb. 15, 2011.
Official Communication in Japanese Application No. 2012-272106, dated Dec. 3, 2013.
Official Communication in Japanese Application No. 2012-272106, dated May 26, 2014.
International Search Report and Written Opinion in International Application No. PCT/US2005/003753, dated Dec. 5, 2006.
International Preliminary Report and Written Opinion in International App No. PCT/US2005/003753, dated Jan. 9, 2007.
Official Communication in European Application No. 08730413.5, dated Feb. 16, 2012.
International Search Report and Written Opinion in International Application No. PCT/US2008/054607, dated Jul. 10, 2008.
International Preliminary Report on Patentability in International Application No. PCT/US2008/054607, dated Sep. 3, 2009.
Official Communication in Australian Application No. 2011292297, dated Jul. 10, 2013.
International Search Report and Written Opinion in International Application No. PCT/US2011/047432, dated Dec. 12, 2011.
International Preliminary Report on Patentability in International Application No. PCT/US2011/047432, dated Feb. 28, 2013.
International Search Report in International Application No. PCT/US2012/026470, dated May 30, 2012.
International Preliminary Report on Patentability and Written Opinion in International Application No. PCT/US2012/026470, dated Sep. 6, 2013.
International Search Report and Written Opinion in International Application No. PCT/US2012/026472, dated Jun. 20, 2012.
International Preliminary Report on Patentability and Written Opinion in International Application No. PCT/US2012/026472, dated Mar. 12, 2014.
International Search Report and Written Opinion in International Application No. PCT/US2014/019325, dated Jun. 17, 2014.
Official Communication in Japanese Application No. 2009-074336, dated Feb. 15, 2011.
International Search Report in International Application No. PCT/CA2002/000193 filed Feb. 15, 2002, dated Jun. 18, 2002.
International Search Report and Written Opinion in International Application No. PCT/US2004/028094, dated May 16, 2005.
International Search Report in International Application No. PCT/US2005/000987 filed Jan. 13, 2005, dated May 24, 2005.
International Preliminary Report on Patentability in International Application No. PCT/US2005/000987 filed Jan. 13, 2005, dated Jan. 17, 2006.

(56) References Cited

OTHER PUBLICATIONS

Notice of Acceptance in Australian Application No. AU2013237744, dated Apr. 23, 2015.
Official Communication in Canadian Application No. 2,803,783, dated Sep. 29, 2014.
Official Communication in Canadian Application No. 2,803,783, dated Aug. 5, 2015.
Official Communication in Japanese Application No. 2012-272106, dated Feb. 23, 2015.
Official Communication in European Application No. 14177951.2, dated Nov. 13, 2014.
Official Communication in European Application No. 11818586.7, dated Nov. 6, 2014.
Official Communication in Japanese Application No. 2013-524882, dated Mar. 2, 2015.
Official Communication in Australian Application No. AU2012222229, dated Aug. 21, 2015.
Official Communication in Australian Application No. AU2012222230, dated Aug. 21, 2015.
International Search Report and Written Opinion in International Application No. PCT/US2014/019302, dated May 18, 2015.
International Preliminary Report on Patentability and Written Opinion in International Application No. PCT/US2014/019325, dated Sep. 24, 2015.
International Search Report and Written Opinion in International Application No. PCT/US2014/056598, dated Dec. 29, 2014.
International Preliminary Report on Patentability in International Application No. PCT/US2004/028094, dated Feb. 25, 2013.
ArthroTek, "CurvTek® Bone Tunneling System," User's Manual, 2000, pp. 20.
Ash, H.E., "Proximal Interphalangeal Joint Dimensions for the Design of a Surface Replacement Prosthesis", School of Engineering, University of Durham, Proceedings of the Institution of Mechanical Engineers Part H Journal of Engineering in Medicine Feb. 1996, vol. 210, No. 2, pp. 95-108.
Beaman, MD et al., "Substance P Innervation of Lumbar Spine Facet Joints", Spine, 1993, vol. 18, No. 8, pp. 1044-1049.
Butterman, et al., "An Experimental Method for Measuring Force on the Spinal Facet Joint: Description and Application of the Method", Journal of Biomechanical Engineering, Nov. 1991, vol. 113, pp. 375-386.
Cruess et al., "The Response of Articular Cartilage to Weight-Bearing Against Metal", The Journal of Bone and Joint Surgery, Aug. 1984, vol. 66-B, No. 4, pp. 592-597.
Dalldorf et al., "Rate of Degeneration of Human Acetabular Cartilage after Hemiarthroplasty", The Journal of Bone and Joint Surgery, Jun. 1995, vol. 77. No. 6, pp. 877-882.
Frost, Harold M., "From Wolff's Law to the Utah Paradigm: Insights About Bone Physiology and Its Clinical Applications", The Anatomical Record, 2001, vol. 262, pp. 398-419.
Kurtz, PhD et al., "Isoelastic Polyaryletheretherketone Implants for Total Joint Replacement", PEEK Biomaterials Handbook, Ch. 14, 2012, pp. 221-226.
Meisel et al., "Minimally Invasive Facet Restoration Implant for Chronic Lumbar Zygapophysial Pain: 1-Year Outcomes", Annals of Surgical Innovation and Research (ASIR), 2014, vol. 8, No. 7, pp. 6.
Panjabi, PhD et al., "Articular Facets of the Human Spine: Quantitative Three-Dimensional Anatomy", Spine, 1993, vol. 18, No. 10, pp. 1298-1310.
Parteq Innovations, "Facet Joint Implants & Resurfacing Devices," Technology Opportunity Bulletin, Tech ID 1999-012, Queen's University, Ontario Canada, pp. 2.
Ravikumar et al., "Internal Fixation Versus Hemiarthroplasty Versus Total Hip Arthroplasty for Displaced Subcapital Fractures of Femur—13 year Results of a Prospective Randomised Study", International Journal of the Care of the Injured (INJURY), 2000, vol. 31, pp. 793-797.
Schendel et al., "Experimental Measurement of Ligament Force, Facet Force, and Segment Motion in the Human Lumbar Spine", Journal of Biomechanics, 1993, vol. 26, No. 4/5, pp. 427-438.
Tanno et al., "Which Portion in a Facet is Specifically Affected by Articular Cartilage Degeneration with Aging in the Human Lumbar Zygapophysial Joint?", Okajimas Folia Anatomica Japonica, May 2003, vol. 80, No. 1, pp. 29-34.
Official Communication in Australian Application No. AU2015205875, dated Apr. 2, 2016.
Official Communication in Australian Application No. AU2015205875, dated Jun. 15, 2016.
Official Communication in Canadian Application No. 2,803,783, dated Jul. 7, 2016.
Official Communication in Canadian Application No. 2,803,783, dated Apr. 5, 2017.
Official Communication in European Application No. 14175088.5, dated Nov. 18, 2015.
Official Communication in European Application No. 16180368.9, dated Mar. 31, 2017.
Official Communication in Japanese Application No. 2012-272106, dated Nov. 2, 2015.
Official Communication in Australian Application No. 2014277721, dated Sep. 8, 2016.
Official Communication in Australian Application No. 2014277721, dated Jan. 9, 2017.
Official Communication in European Application No. 11818586.7, dated Feb. 3, 2017.
Official Communication in Japanese Application No. 2013-524882, dated Nov. 16, 2015.
Official Communication in Japanese Application No. 2015-242990, dated Dec. 12, 2016.
Official Communication in Australian Application No. AU2012222229, dated May 11, 2016.
Official Communication in European Application No. EP12749447.4, dated Jan. 4, 2017.
Official Communication in European Application No. EP12749447.4, dated Apr. 4, 2017.
Official Communication in European Application No. 12749251.0, dated Jan. 4, 2017.
Official Communication in Japanese Application No. JP 2013-555591, dated Jan. 4, 2016.
Official Communication in Japanese Application No. JP 2013-555592, dated Dec. 7, 2015.
Official Communication in Japanese Application No. JP 2013-555592, dated Aug. 8, 2016.
Official Communication in European Application No. 14774714.1, dated Oct. 21, 2016.
Official Communication in European Application No. 14776445.0, dated Nov. 7, 2016.
Official Communication in European Application No. 14850082.0, dated Aug. 31, 2016.
International Preliminary Report on Patentability and Written Opinion in International Application No. PCT/US2014/056598, dated Apr. 7, 2016.
International Search Report and Written Opinion in International Application No. PCT/US2015/050441, dated Dec. 28, 2015.
International Preliminary Report on Patentability and Written Opinion in International Application No. PCT/US2015/050441, dated Mar. 30, 2017.
International Search Report and Written Opinion in International Application No. PCT/US2016/013062, dated Mar. 16, 2016.

* cited by examiner

METHODS AND APPARATUS FOR STABILIZING BONE

CROSS-REFERENCE TO RELATED APPLICATIONS

The present application is a continuation of U.S. application Ser. No. 14/256,532, filed Apr. 18, 2014, which is a divisional of U.S. application Ser. No. 13/033,791, filed Feb. 24, 2011, the disclosures of each of these applications are incorporated by reference herein in their entirety.

BACKGROUND

Some embodiments described herein relate generally to methods and apparatus for stabilizing bone, for example, stabilizing vertebrae by securing the articular processes of the vertebrae.

Traumatic, inflammatory, and degenerative disorders of the spine can lead to severe pain and loss of mobility. One source of back and spine pain is related to degeneration of the facets of the spine or facet arthritis. Bony contact or grinding of degenerated facet joint surfaces can play a role in some pain syndromes. While many technological advances have focused on the intervertebral disc and artificial replacement or repair of the intervertebral disc, little advancement in facet repair has been made. Facet joint and disc degeneration frequently occur together. Thus, a need exists to address the clinical concerns raised by degenerative facet joints.

The current standard of care to address the degenerative problems with the facet joints is to fuse the two adjacent vertebrae. By performing this surgical procedure, the relative motion between the two adjacent vertebrae is stopped, thus stopping motion of the facets and any potential pain generated as a result thereof. Procedures to fuse two adjacent vertebrae often involve fixation and/or stabilization of the two adjacent vertebrae until the two adjacent vertebrae fuse.

Injuries and/or surgical procedure on and/or effecting other bones can also result in the desire to fixate and/or stabilize a bone until the bone, or bone portions, can fuse, for example, to stabilize a sternum after heart surgery, to stabilize a rib after a break, etc. Current procedures to fixate and/or stabilize adjacent vertebrae and/or other bones can be slow and/or complex.

Accordingly, a need exists for an apparatus and a procedure to quickly and/or easily stabilize and/or fixate a bone.

SUMMARY

In some embodiments, a method comprises forming a lumen in a first bone portion and forming a lumen in a second bone portion. The method further includes inserting a portion of a flexible fastening band through the lumen in the first bone portion and through the lumen in the second bone portion, and inserting the portion of the flexible fastening band into a fastening mechanism monolithically formed with the flexible fastening band. The method further includes advancing the portion of the flexible fastening band through the fastening mechanism until the first bone portion and the and the second bone portion are stabilized.

DETAILED DESCRIPTION

In some embodiments, a method comprises disposing a portion of a flexible fastening band into contact with a first bone portion and into contact with a second bone portion. The portion of the flexible fastening band having a substantially uniform shape configured to substantially compliment a shape of the first bone portion and a shape of the second bone portion. The method further includes inserting the portion of the flexible fastening band into a fastener and advancing the portion of the flexible fastening band through the fastener until the first bone portion and the and the second bone portion are stabilized.

In some embodiments, an apparatus includes a flexible elongate body including a proximal end portion, a first portion, a second portion, a reinforcement portion, and a distal end portion. The distal end portion of the flexible elongate body includes a fastener configured to accept the proximal end portion and the first portion. The second portion includes a first material, and the reinforcement portion includes a second material, different from the first material and stronger than the first material. The reinforcement piece is disposed within at least a portion of the second portion.

In some embodiments, an apparatus comprises a flexible elongate body including a proximal end portion, a first portion, a second portion mutually exclusive from and distal to the first portion, and a distal end portion. The apparatus further comprises a fastener configured to accept the proximal end portion and the first portion. The first portion of the flexible elongate body having a length and a substantially uniform first shape and the second portion of the flexible elongate body having a length and a substantially uniform second shape, different from the first shape, that is configured to substantially compliment a shape of first bone portion and a shape of a second bone portion. The fastener configured to receive the first portion of the flexible elongate body when the second portion of the flexible elongate body is disposed in contact with the first bone portion and in contact with the second bone portion.

As used in this specification, the singular forms "a," "an" and "the" include plural referents unless the context clearly dictates otherwise. Thus, for example, the term "a ratchet" is intended to mean a single ratchet or a combination of ratchets. As used in this specification, a substance can include any biologic and/or chemical substance, including, but not limited to, medicine, adhesives, etc. While exemplary references are made with respect to vertebra, in some embodiments another bone can be involved. While specific reference may be made to a specific vertebra and/or subset and/or grouping of vertebrae, it is understood that any vertebra and/or subset and/or grouping, or combination of vertebrae can be used.

Figure 1:
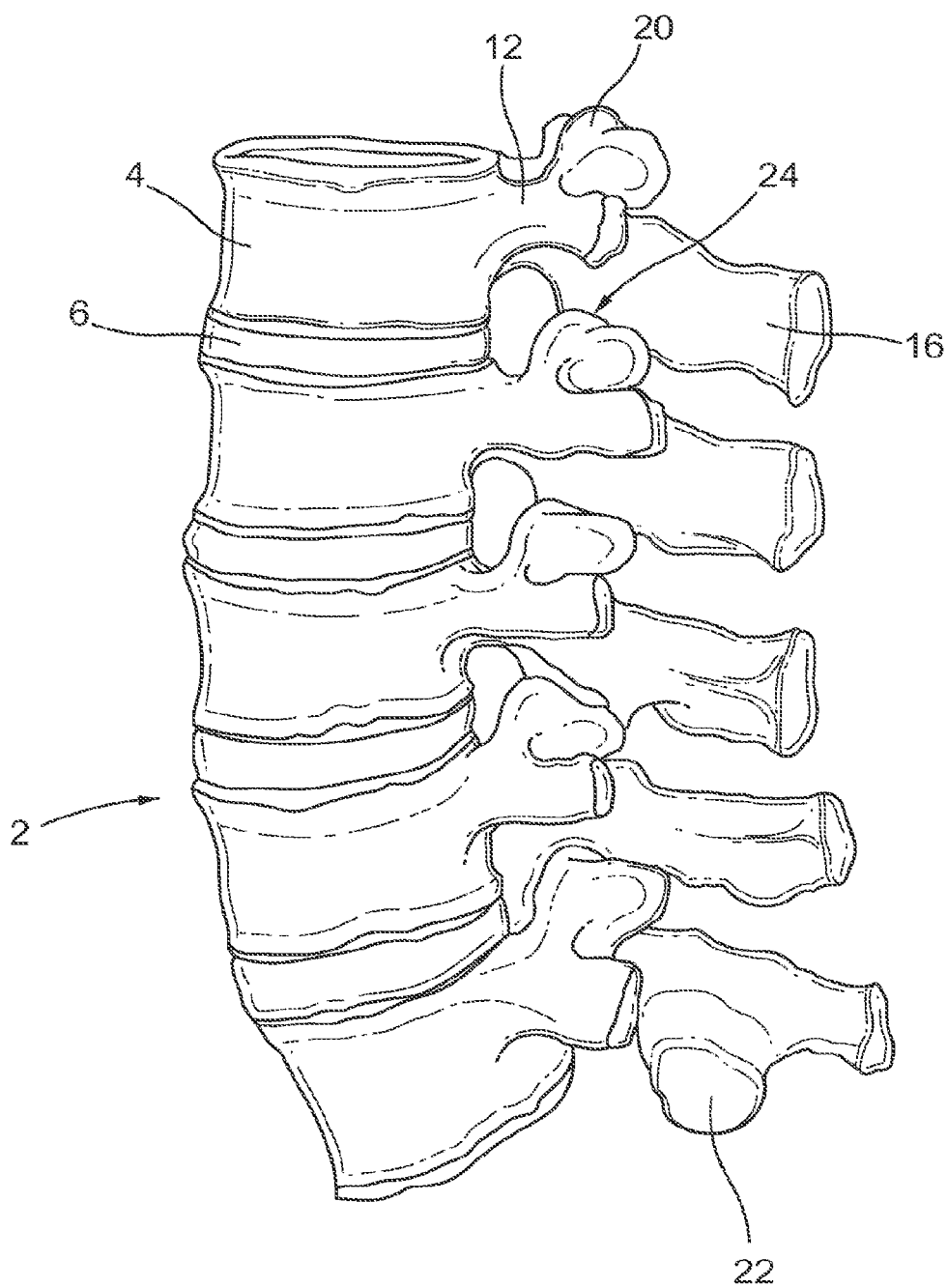
FIG. 1 is a lateral elevational view of a portion of the vertebral column.
Figure 2A:
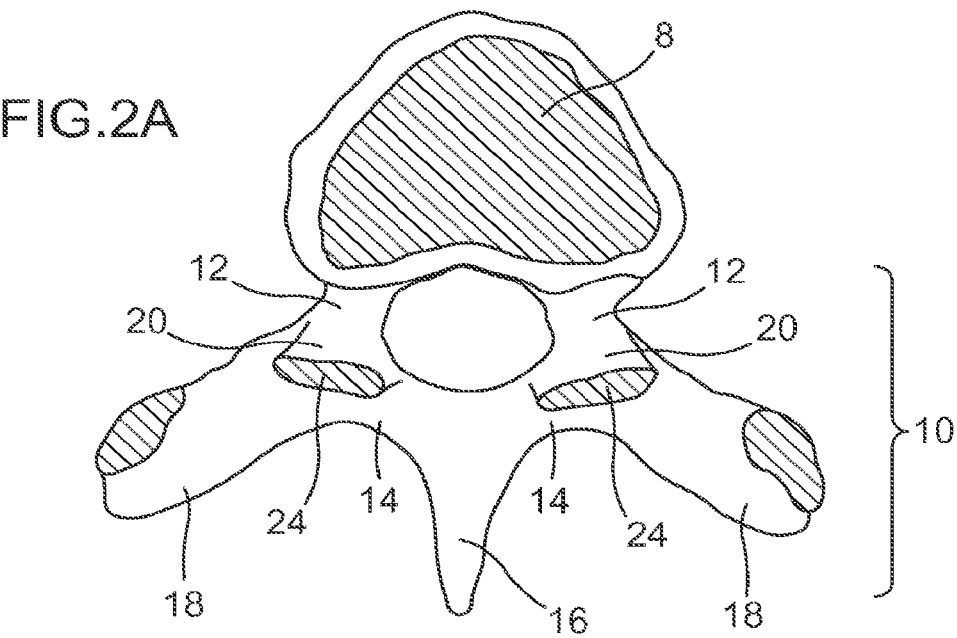
FIG. 2A is a schematic superior view of an isolated thoracic vertebra.
Figure 2B:
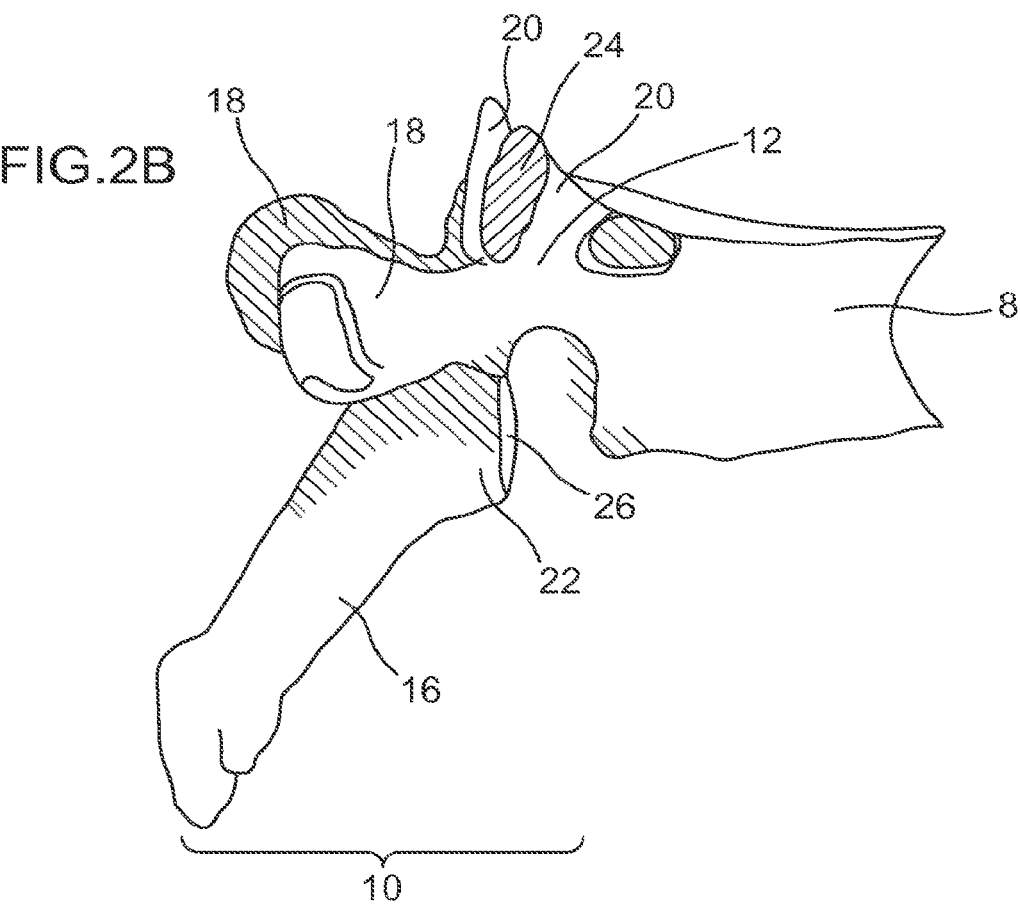
FIG. 2B are schematic side view of an isolated thoracic vertebra.
Figure 3A:
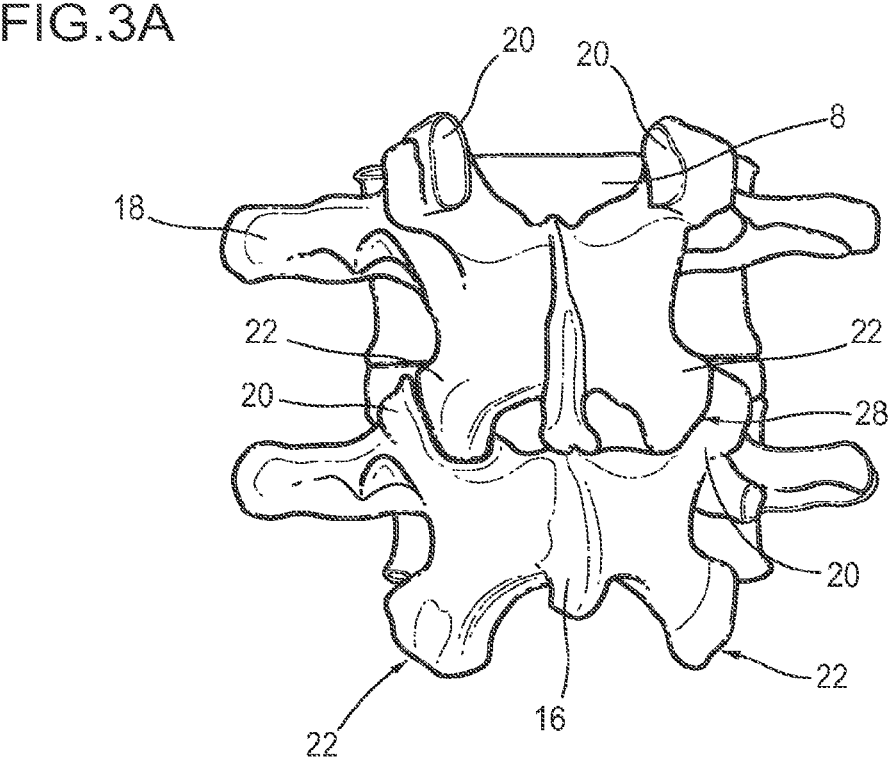
FIG. 3A is a schematic posterior elevational view of a portion of the vertebral column.
Figure 3B:
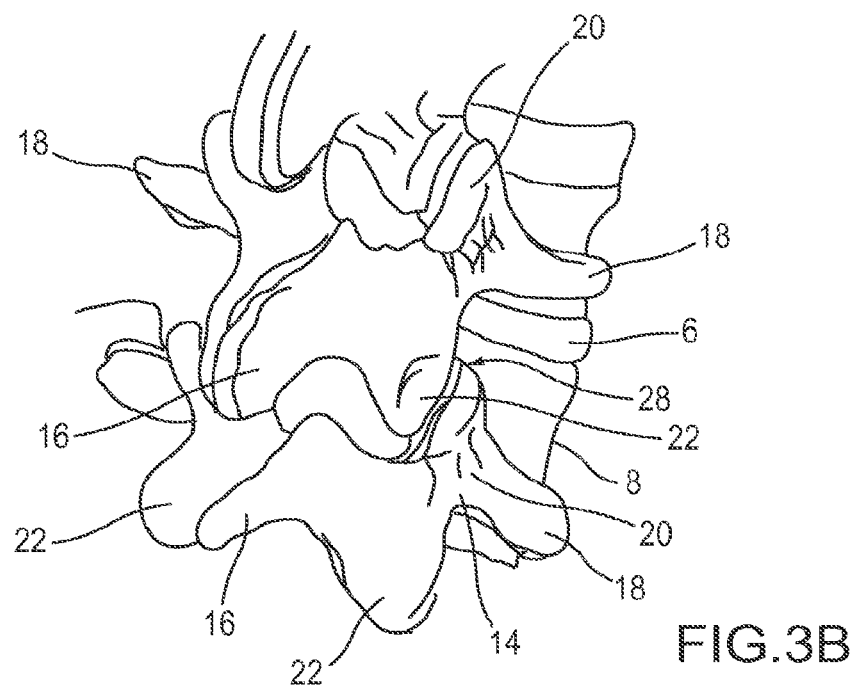
FIG. 3B is a posterior-oblique elevational view of a portion of the vertebral column.
Figure 4A:
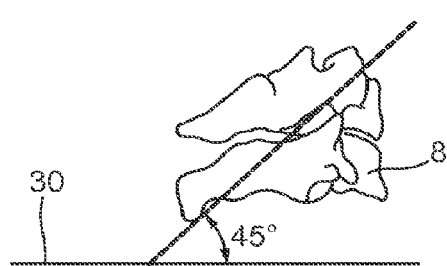
FIG. 4A is a schematic side view of a facet joint in the cervical vertebrae.
Figure 4B:
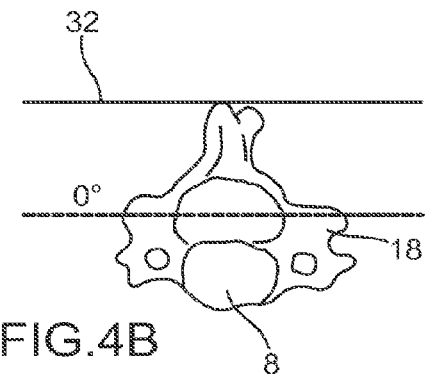
FIG. 4B is a schematic superior view of a facet joint in the cervical vertebrae.

As shown in FIG. 1, the vertebral column 2 comprises a series of alternating vertebrae 4 and fibrous discs 6 that provide axial support and movement to the upper portions of the body. The vertebral column 2 typically comprises thirty-three vertebrae 4, with seven cervical (C1-C7), twelve thoracic (T1-T12), five lumbar (L1-15), five fused sacral (S1-S5) and four fused coccygeal vertebrae. FIGS. 2A and 2B depict a typical thoracic vertebra. Each vertebra includes an anterior body 8 with a posterior arch 10. The posterior arch 10 comprises two pedicles 12 and two laminae 14 that join posteriorly to form a spinous process 16. Projecting from each side of the posterior arch 10 is a transverse 18, superior 20 and inferior articular process 22. The facets 24, 26 of the superior 20 and inferior articular processes 22 form facet joints 28 with the articular processes of the adjacent vertebrae (see FIGS. 3A and 3B). The facet joints are true synovial joints with cartilaginous surfaces and a joint capsule.

Figure 5A:
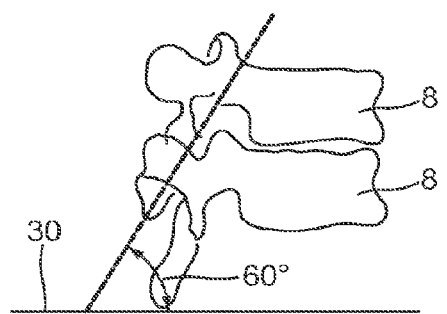
FIG. 5A is a schematic side view of a facet joint in the thoracic vertebrae.
Figure 5B:
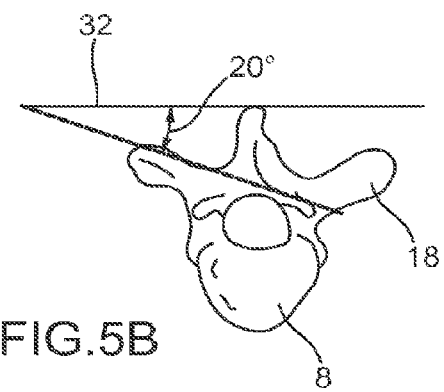
FIG. 5B is a schematic superior view of a facet joint in the thoracic vertebrae.
Figure 6A:
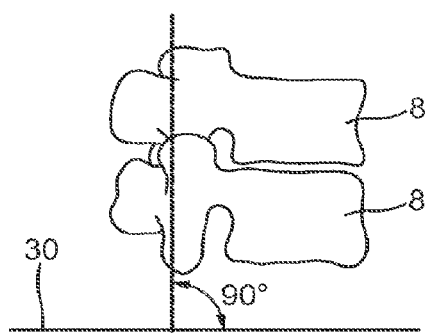
FIG. 6A is a schematic side view of a facet joint in the lumbar vertebrae.
Figure 6B:
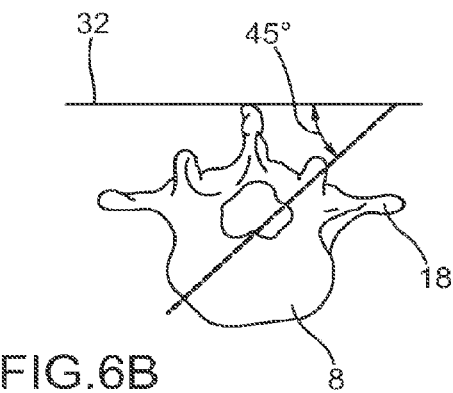
FIG. 6B is a schematic superior view of a facet joint in the lumbar vertebrae.

The orientation of the facet joints vary, depending on the level of the vertebral column. In the C1 and C2 vertebrae, for example the facet joints are parallel to the transverse plane. FIGS. 4A to 6B depict examples of the orientations of the facet joints at different levels of the vertebral column. In the C3 to C7 vertebrae examples shown in FIGS. 4A and 4B, the facets are oriented at a 45-degree angle to the transverse plane 30 and parallel to the frontal plane 32, respectively. This orientation allows the facet joints of the cervical vertebrae to flex, extend, lateral flex and rotate. At a 45-degree angle in the transverse plane 30, the facet joints of the cervical spine can guide, but do not limit, the movement of the cervical vertebrae. FIGS. 5A and 5B depict examples of the thoracic vertebrae, where the facets are oriented at a 60-degree angle to the transverse plane 30 and a 20-degree angle to the frontal plane 32, respectively. This orientation is capable of providing lateral flexion and rotation, but only limited flexion and extension. FIGS. 6A and 6B illustrate examples of the lumbar region, where the facet joints are oriented at 90-degree angles to the transverse plane 30 and a 45-degree angle to the frontal plane 32, respectively. The lumbar vertebrae are capable of flexion, extension and lateral flexion, but little, if any, rotation because of the 90-degree orientation of the facet joints in the transverse plane. The actual range of motion along the vertebral column can vary considerably with each individual vertebra.

In addition to guiding movement of the vertebrae, the facet joints also contribute to the load-bearing ability of the vertebral column. One study by King et al. Mechanism of Spinal Injury Due to Caudocephalad Acceleration, Orthop. Clin. North Am., 6:19 1975, found facet joint load-bearing as high as 30% in some positions of the vertebral column. The facet joints may also play a role in resisting shear stresses between the vertebrae. Over time, these forces acting on the facet joints can cause degeneration and arthritis.

Figure 7:
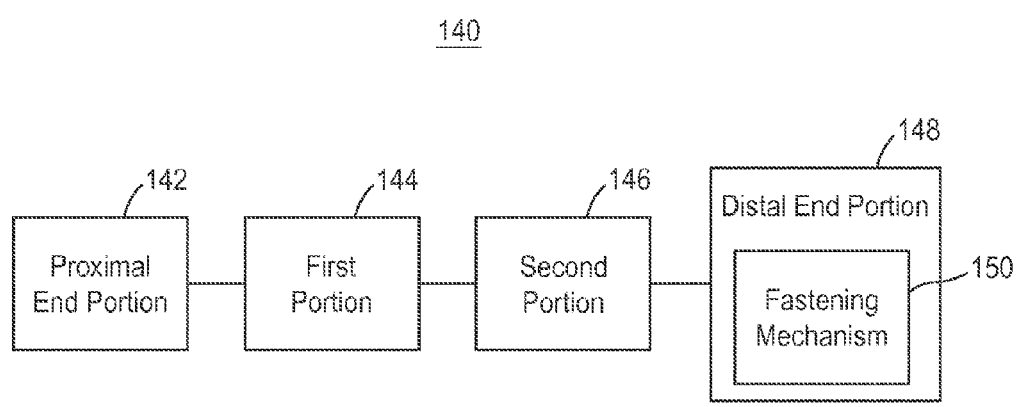
FIG. 7 is a block diagram of a flexible fastening band according to an embodiment.

In some embodiments described herein, a flexible fastening band can be used to stabilize and/or fixate a first vertebra to a second vertebra to reduce the pain, to reduce further degradation of a spine, or of a specific vertebra of a spine, and/or until the first vertebra and the second vertebra have fused. FIG. 7 depicts a block diagram of a flexible fastening band ("band") 140. Band 140 includes a flexible elongate body including a proximal end portion 142, a first portion 144, a second portion 146, and a distal end portion 148 that includes a fastening mechanism 150 (alternatively referred to herein as a fastener). In some embodiments, band 140 can include a third portion (not shown in FIG. 7). In some embodiments, band 140 can include a spacer (not shown in FIG. 7). In some embodiments, the fastening mechanism can be separate from the distal end portion (see, e.g., FIGS. 26-30). Band 140 can be configured to stabilize a first vertebra (not shown in FIG. 7) and/or a second vertebra (not shown in FIG. 7). Specifically, band 140 can be configured to stabilize the first vertebra and/or second vertebra by securing an articular process of the first vertebra to an articular process of a second vertebra. More specifically, band 140 can be configured to stabilize the first vertebra and/or a second vertebra by securing an articular process of the first vertebra to an articular process of a second vertebra by securing a facet of the articular process of the first vertebra with a facet of the articular process of the second vertebra. In some embodiments, band 140 can be removed from the vertebra, e.g. by cutting, breaking, or otherwise releasing band 140. In this manner, should a band fail, a replacement band can be inserted. Similarly, should the band be deemed ineffective for a particular patient, the band can be removed and an alternate treatment can be chosen without incurring permanent fusion of the vertebra. As will be described in more detail herein, band 140 can be monolithically formed or separately formed. Band 140 can include any biocompatible material, e.g., stainless steel, titanium, PEEK, nylon, etc.

Proximal end portion 142 is configured to pass through a lumen formed through a vertebra and a lumen formed through an adjacent vertebra, and to pass through fastening mechanism 150 of the distal end portion 148. In some embodiments, proximal end portion 142 can be shaped to increase the ease of inserting proximal end portion 142 into fastening mechanism 150, e.g., proximal end portion 142 can be tapered, rounded, and/or angled, etc, to reduce at least a portion of a cross-sectional area of proximal end portion 142.

First portion 144 can extend for a length between proximal end portion 142 and second portion 146, and can have a substantially uniform shape. The first portion 144 can have, for example, a substantially cuboidal shape, or a substantially cylindrical shape. In some embodiments, the length of first portion 144 can be more than twice the length of second portion 146. In some embodiments, the cross-sectional area of the first portion 144 can be smaller than the cross-sectional area of the second portion 146. In some embodiments, the cross-sectional area of first portion 144 can be less than a cross-sectional area of a lumen defined by the fastening mechanism 150. First portion 144 can include a gear rack (not shown in FIG. 7) configured to engage a ratchet (not shown in FIG. 7) of the fastening mechanism 150. The gear rack can be configured to allow first portion 144 to travel through fastening mechanism 150 in only one direction. First portion 144 can be monolithically formed with second portion 146. In some other embodiments, the first portion can be separately formed from the second portion. First portion 144 can be configured to be slidably disposed in a lumen of second portion 146.

Second portion 146 can have a length between first portion 144 and distal end portion 148, and can include a substantially uniform shape. In embodiments including the third portion, second portion 146 can have a length between first portion 144 and the third portion. Second portion 146 can have, for example, a substantially cuboidal shape or a substantially cylindrical shape. First portion 144 and second portion 146 can have the same or different shapes, e.g., first portion 144 and second portion 146 can both be substantially cuboidal (see, e.g., band 240 in FIG. 8), first portion 144 and second portion 146 can both be substantially cylindrical (see, e.g., band 840 in FIG. 18), first portion 144 can be substantially cuboidal while second portion 146 can be substantially cylindrical (see, e.g., band 440 in FIG. 12), or first portion 144 can be substantially cylindrical while second portion 146 can be substantially cuboidal (not shown). In some embodiments, the length of second portion 146 can be less than half the length of first portion 144. In some embodiments, the cross-sectional area of the second portion 146 can be greater than the cross-sectional area of the first portion 144. In some embodiments, the cross-sectional area of second portion 146 can be greater than a cross-sectional area of a lumen defined by the fastening mechanism 150. In this manner, as a portion of band 140 is advanced through fastening mechanism 150, the cross-sectional area of second portion 146 can prevent band 140 from advancing beyond the first portion 144. Second portion 146 can include a gear rack (not shown in FIG. 7) configured to engage the ratchet of the fastening mechanism 150. The gear rack can be configured to allow second portion 46 to travel through fastening mechanism 150 in only one direction. Second portion 146 can be monolithically formed with first portion 144. In some embodiments, the second portion can be separately formed from the first portion. Second portion 146 can define a lumen configured to slidably accept first portion 144.

Distal end portion 148 includes a fastening mechanism 150 configured to accept at least a portion of proximal end portion 142, first portion 144, and/or second portion 146. In some embodiments, distal end portion 148, second portion 146, first portion 144, and proximal end portion 142 can be monolithically formed. Fastening mechanism 150 includes a lumen (not shown in FIG. 7) configured to accept at least a portion of proximal end portion 142, a portion of first portion 142, and/or a portion of second portion 146. In some embodiments, the cross-sectional area of the lumen of fastening mechanism 150 is smaller than the cross-sectional area of second portion 146. In this manner, second portion 146 can be prevented from advancing through fastening mechanism 150. In some embodiments, fastening mechanism can include a ratchet (not shown in FIG. 7) configured to engage the gear rack of the first portion 144 and/or second portion 146. In this manner, the fastening mechanism can allow first portion 144 and/or second portion 146 to advance through fastening mechanism 150 in only one direction.

In some embodiments, at least one of distal end portion 148, second portion 146, first portion 144, and proximal end portion 142 can be formed separately from the other(s) of distal end portion 148, second portion 146, first portion 144, and proximal end portion 142. Said another way, and by way of example, distal end portion 148, first portion 144, and proximal end portion 142 can be monolithically formed together, while second portion 146 can be separately formed. In this manner, band 140 can include an initial second portion 146 configured to be replaced and/or covered with a replacement second portion 146. By way of a first example, initial second portion 146 can be monolithically formed with first portion 144 and replacement second portion 146 can be slidably disposed over initial second portion 146. By way of a second example, initial second portion 146 can be separately formed from first portion 144, can be removed from band 140, and replacement second portion 146 can be slidably disposed over first portion 144. By way of a third example, initial second portion 146 can be separately or monolithically formed from first portion 144, and replacement second portion 146 can be slidably disposed over first portion 144 and initial second portion 146. In some embodiments, initial second portion 146 and replacement second portion 146 can have the same shape, e.g., initial second portion 146 can include a substantially cylindrical shape and replacement second portion 146 can include a substantially cylindrical shape. In some embodiments, initial second portion 146 and replacement second portion 146 can have different shapes, e.g., initial second portion 146 can include a substantially cuboidal shape and replacement second portion 146 can include a substantially cylindrical shape.

In some embodiments, the shape of first portion 144 and the shape of second portion 146 can be determined based on the shape of an artificial lumen formed through a articular process of a vertebra. By way of example, if the shape of the artificial lumen is cuboidal, the shape of the of the first portion 144 and the shape of the second portion 146 can be cuboidal to allow the first portion 144 and the second portion 146 to slidably advance through the artificial lumen. By way of a second example, if the shape of the artificial lumen is cylindrical, the shape of the first portion 144 and the shape of the second portion 146 can be either cuboidal or cylindrical. Continuing with the second example, the shape of the first portion 144 can be cuboidal to allow the first portion 144 to advance easily through the artificial lumen, while the shape of the second portion 146 can be cylindrical to allow the second portion 146 to fit more tightly within the artificial lumen as compared to a cuboidal shape.

In some embodiments, the shape of the first portion 144 and the shape of the second portion 146 can be determined based on characteristics of the bone or bone portion against which the first portion 144 and the second portion 146 may contact. By way of example, while first portion 144 and/or second portion 146 can be substantially cuboidal, edges of the first portion 144 and/or the second portion 146 can be rounded, partially rounded, and/or otherwise shaped to compliment the shape of a bone or bone portion, and/or to reduce digging or grinding into the bone or bone portion. In this manner, use of band 140 may cause little or no damage to the bone or bone portions contacted by band 140.

In some embodiments, band 140 can include a third portion (not shown in FIG. 7). The third portion can have a length between second portion 146 and distal end portion 150, and can have a substantially uniform shape. In some embodiments, the third portion can have, for example, a substantially cuboidal shape or a substantially cylindrical shape. In some embodiments, the length of the third portion can be less than half the length of first portion 144. The third portion can be monolithically formed with first portion 144 and/or the second portion 146. In some other embodiments, the first portion can be separately formed from the second portion and/or the first portion.

While each of first portion 144, second portion 146, and the third portion can be a substantially uniform shape, in some embodiments any one of first portion 144, second portion 146, and the third portion can include a transition portion to transition band 140 from a first substantially uniform shape to a second substantially uniform shape. By way of example, in some embodiments, first portion 144 and the third portion can be substantially cuboidal and second portion 146 can be substantially cylindrical. In this example, second portion 146 can include an angled, conical, or other shaped transition portion (see, e.g., second portion 446 in FIG. 13).

In some embodiments, the band can include a spacer (not shown). The spacer can be similar to, and have similar features to the embodiments of the prosthesis shown and described in U.S. patent application Ser. No. 12/859,009; filed Aug. 18, 2010, and titled "Vertebral Facet Joint Drill and Method of Use" (referred to as "the '009 application"), and is incorporated herein by reference in its entirety. As described in the '009 patent, the spacer can be implanted and deployed to restore the space between facets of a superior articular process of a first vertebra and an inferior articular process of an adjacent vertebra. As described herein, the spacer can be implanted and deployed to help stabilize adjacent vertebrae with adhesives, and/or can be implanted and deployed to deliver a medication. In such embodiments, the spacer can be, for example, substantially disc shaped. In other embodiments, the spacer can be other shapes, e.g., square, elliptical, or any other shape. The spacer can include a first side and a second side. The first side and/or the second side can be, for example, convex, concave, or flat. Said another way, the first side of the spacer can be concave, convex, or flat, and the second side of the spacer can be concave, convex, or flat, for example, the first side can be concave and the second side concave, the first side can be concave and the second side convex, etc. The spacer can include the same materials as band 140. In some embodiments, the spacer can include substances configured to release medication and/or increase the stability of a vertebra and/or band 140. As discussed above, the substances can is include a medicine(s) and/or an adhesive(s).

Figure 8:
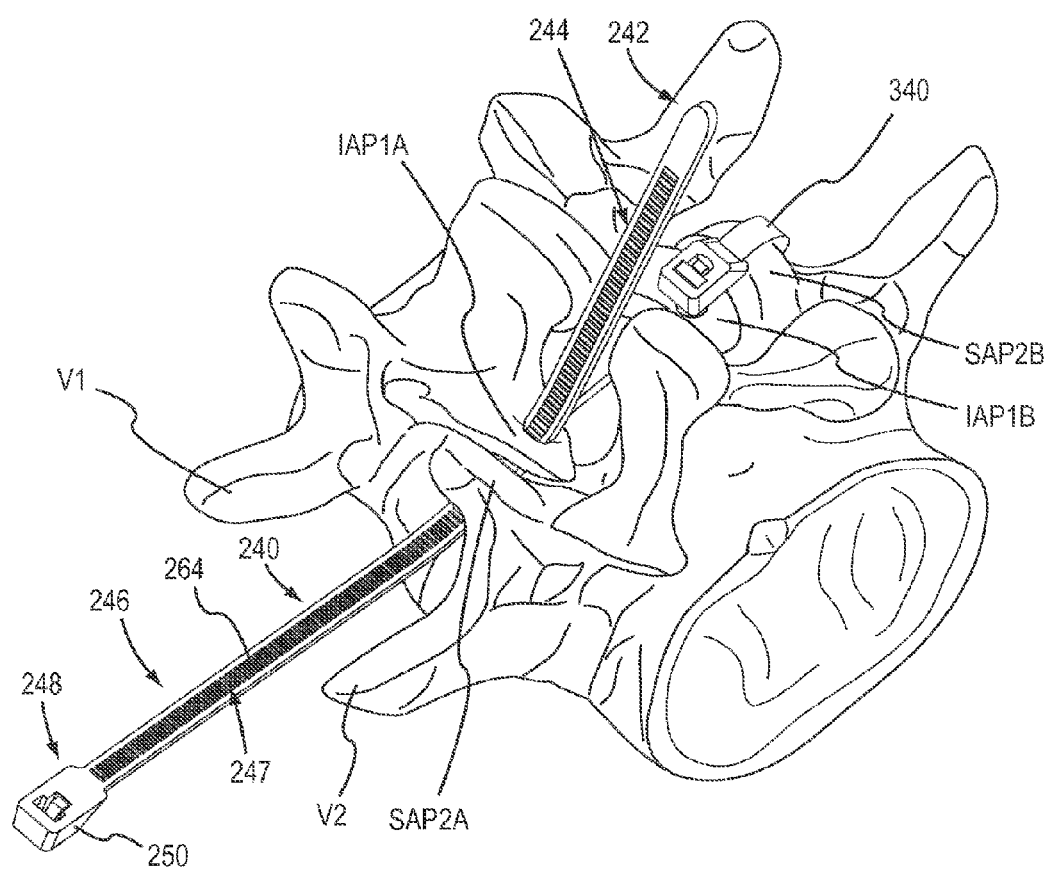
FIGS. 8-10 are posterior perspective views of a portion of the vertebral column depicting a method of stabilizing a vertebra using a flexible fastening band according to an embodiment.
Figure 9:
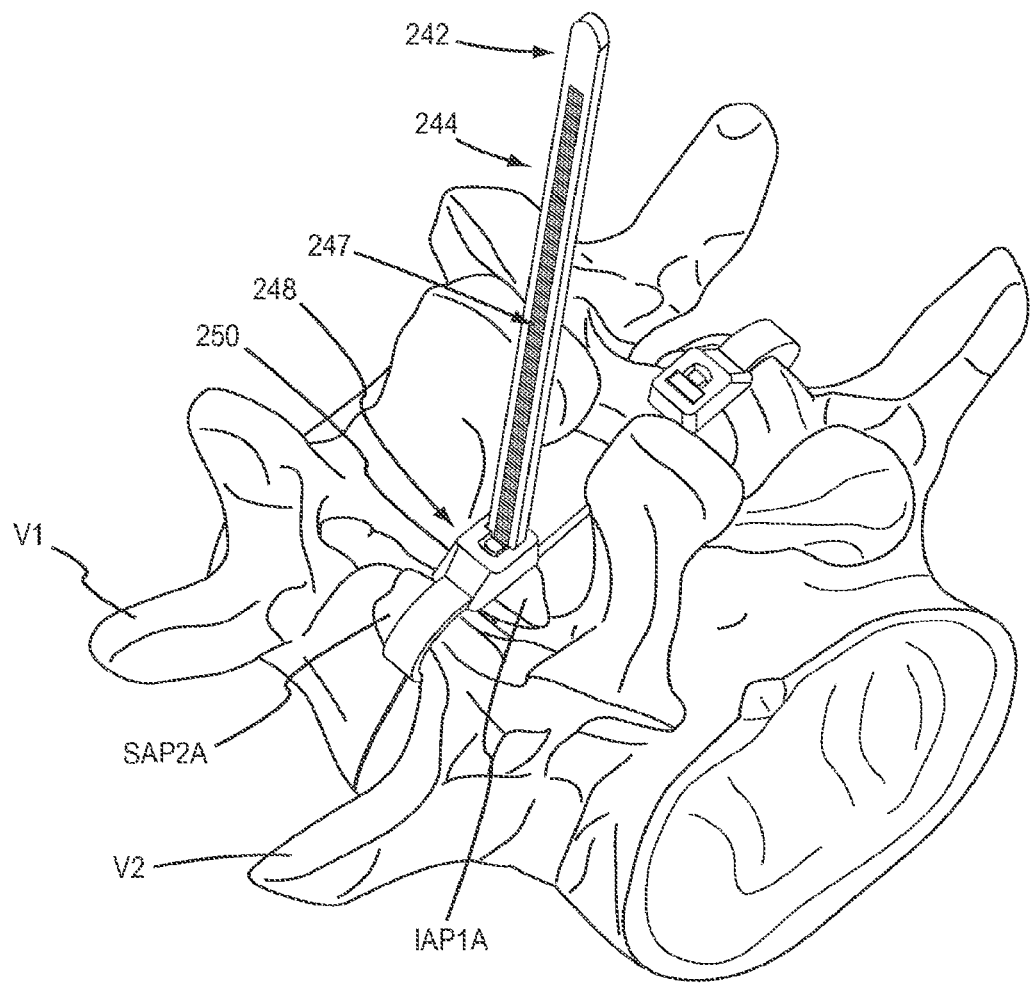
Figure 10:
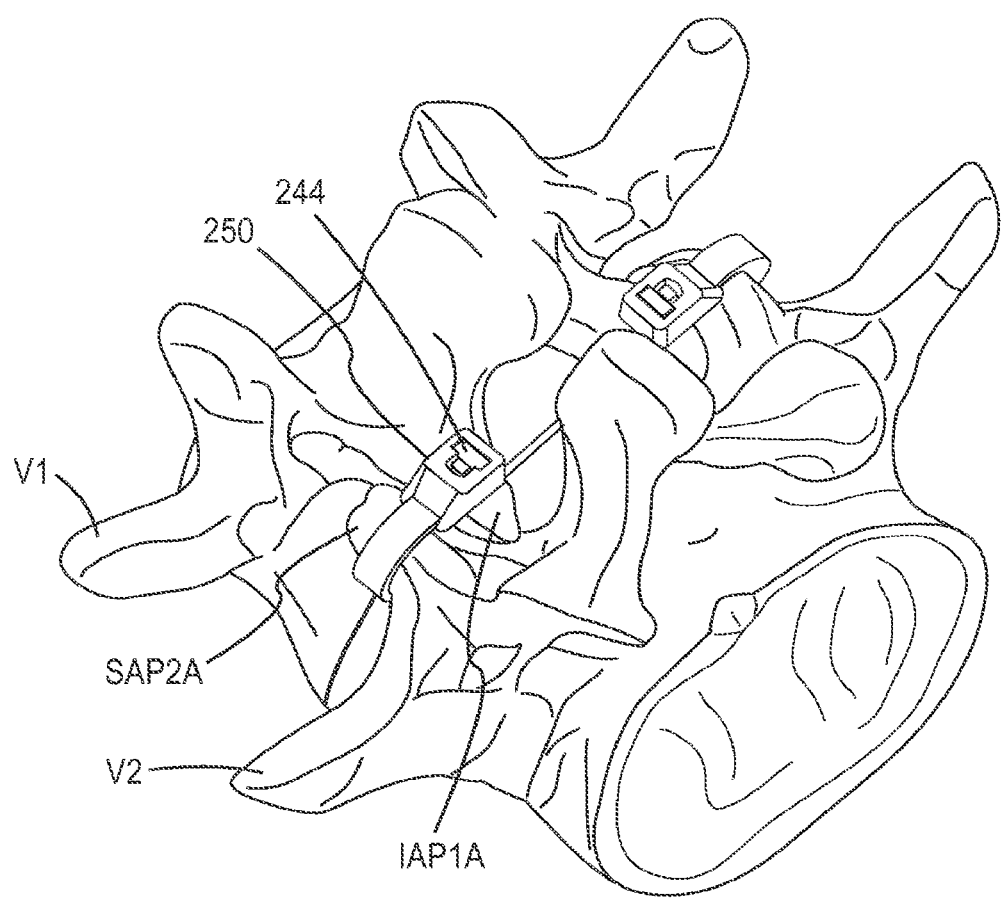

FIGS. 8-10 show posterior perspective views of a portion of the vertebral column during a method for stabilizing adjacent vertebrae using a flexible fastening band ("band") 240 according to an embodiment. As shown in FIG. 8, a band 240 can be used to stabilize a vertebra V1 and vertebra V2 via the inferior articular process IAP1A of vertebra V1 and the superior articular process SAP2A of vertebra V2. Also as shown in FIG. 8, a flexible fastening band ("band") 340 is used to stabilize a vertebra V1 and vertebra V2 via the inferior articular process IAP1B of vertebra V1 and the superior articular process SAP2B of vertebra V2. In some embodiments, vertebra V1 and/or vertebra V2 are stabilized using only one of band 240 or band 340. In some such embodiments, one of band 240 or band 340 can be used to stabilize vertebra V1 and/or vertebra V2 via one of via the inferior articular process IAP1A of vertebra V1 and the superior articular process SAP2A of vertebra V2, or, via the inferior articular process IAP1B of vertebra V1 and the superior articular process SAP2B of vertebra V2. In other such embodiments, one of band 240 or band 340 can be used to stabilize vertebra V1 and/or vertebra V2 via both of the inferior articular process IAP of vertebra V1 and the superior articular process SAP2A of vertebra V2 and, the inferior articular process IAP1B of vertebra V1 and the superior articular process SAP2B of vertebra V2.

Each of band 240 and band 340 can be similar to band 140 described above and can include similar components. By way of example, band 240 includes a proximal end portion 242, a first portion 244, a second portion 246, and a distal end portion 248 including a fastening mechanism 250, and band 340 includes a proximal end portion (not shown in FIG. 8), a first portion, a second portion, and a distal end portion including a fastening mechanism. As shown in FIGS. 8-10, the shapes of first portion 244, the first portion of band 340, second portion 246, and the second portion of band 340 can all be cuboidal. As shown in FIG. 8, band 240 includes a gear rack 247 and gears 264. Each of gears 264 can be wedge shaped to allow each of gears 264 to displace the ratchet of fastening mechanism 250 in only one direction. In some embodiments, gears 264 can be other shapes, such as blocks, etc.

Figure 11:
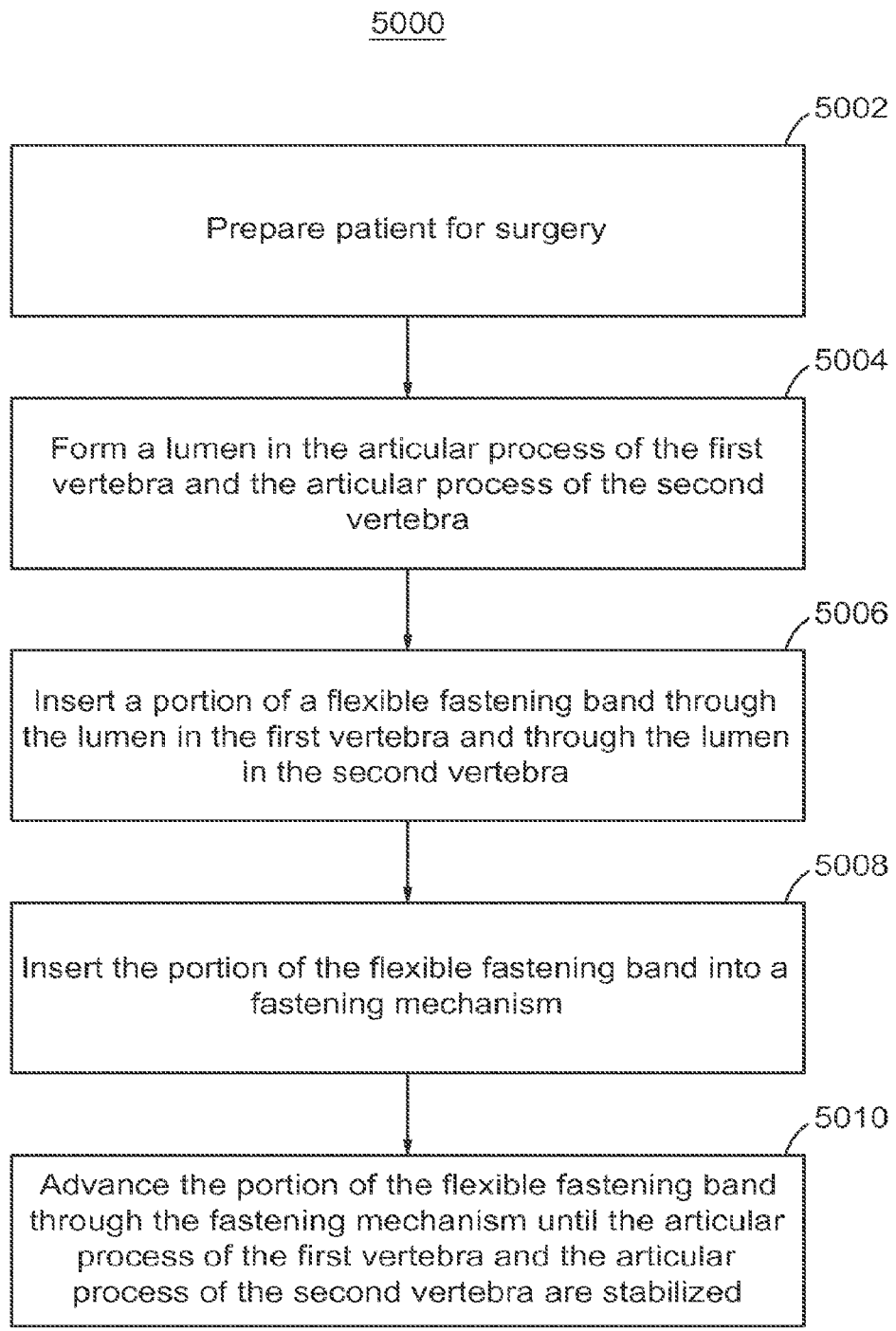
FIG. 11 is a flow chart illustrating a method of using the flexible fastening band depicted FIGS. 8-10.

FIG. 11 depicts a flow chart illustrating a method 5000 of using band 240 and/or band 340. Prior to use of band 240 and/or band 340, a patient can be prepared for surgery, at 5002. Some examples of preparations for surgery are described in the '009 patent. In addition to those procedures described in the '009 application, in some embodiments, the surgical procedure can include direct visualization of the vertebra(e) to be stabilized. Said another way, the medical practitioner can perform the operation without the use of fluoroscopy, and, in this manner, may not have to rely on the inaccuracies and/or inconvenience inherent in fluoroscopic procedures. This direct visualization can be possible due to the small incision necessary for implantation of the band, for example, less than about 25 mm, and due to the ease of implanting and deploying the band. In some embodiments, the surgical procedure used can include forming an opening in body tissue substantially equidistant between a first articular process of the first vertebra and a second articular process of the first vertebra. A tube (not shown) can be inserted through the opening and a proximal end of the tube can be positioned near the lumen of superior articular process SAP2A of vertebra V2. A drill or other device can be used to form a lumen in superior articular process SAP2A of vertebra V2 and inferior articular process IAP1A of vertebra V1, at 5004. Specifically, the drill can be used to form the lumen in a facet of superior articular process SAP2A of vertebra V2 and form the lumen in a facet of inferior articular process IAP1A of vertebra V1. Methods and devices for forming lumens in vertebra are described in the '009 application. The band 240 can be positioned within the tube and can be advanced through the tube until the proximal end portion 242 is positioned near the lumen of superior articular process SAP2A of vertebra V2. In some embodiments, the proximal end of the tube can have a bend to direct the proximal end portion 242 into the lumen of superior articular process SAP2A of vertebra V2. Proximal end portion 242 is inserted into the lumen of superior articular process SAP2A of vertebra V2 and through the lumen of inferior articular process IAP1A of vertebra V1, at 5006, and a portion of first portion 244 is advanced through the lumen of superior articular process SAP2A of vertebra V2 and through the lumen of inferior articular process IAP1A of vertebra V1. The tube can be removed and/or reinserted at various points during the method 5000, including, for example, after the proximal end portion of band 240 is inserted into the lumen formed within the superior articular process SAP2A of vertebra V2, after vertebra V1 and/or Vertebra V2 has been stabilized, or at other points during method 5000. In some embodiments, first portion 244 can be advanced through the lumen of superior articular process SAP2A of vertebra V2 and through the lumen of inferior articular process IAP1A of vertebra V1 such that only second portion 246 is within the lumen of superior articular process SAP2A of vertebra V2 and through the lumen of inferior articular process IAP1A of vertebra V1. In this manner, when the shape of the second portion is substantially similar to the shape of the lumen of the superior articular process of the first vertebra and shape of the lumen of the inferior articular process of second vertebra, the lumen can only be contacted by that portion of the band, for example, the second portion, having the same shape.

As shown in FIG. 9, proximal end portion 242 is inserted into the lumen of fastening mechanism 250 of distal end portion 248, at 5008. In some embodiments, to insert proximal end portion 242 into fastening mechanism 250 of distal end portion 248, a medical practitioner can grasp proximal end 242 and distal end 248, and manually insert proximal end portion 242 into fastening mechanism 250. In other embodiments, one or both of proximal end portion 242 and distal end portion 248 can be grasped with surgical tools (not shown). In such embodiments, the surgical tools can be configured to fit specific band configurations, for example, the surgical tools can be configured to receive distal end 248 without obstructing the lumen of fastening mechanism 250. By way of another example, the surgical tools can be configured to grasp and manipulate proximal end portion 242 and/or first portion 244. A portion of first portion 244 is advanced through the lumen of fastening mechanism 250 of distal end portion 248 until superior articular process SAP2A of vertebra V2 and inferior articular process IAP1A of vertebra V1 are stabilized, at 5010. In some embodiments, a surgical tool can be used to advance first portion 244 through the lumen of fastening mechanism 250. In such embodiments, one portion of the surgical tool can be configured to receive distal portion 248 without obstructing the lumen through fastening mechanism 250, one portion of the surgical tool can be configured to grip and/or advance proximal end portion 242 and or first portion 244. The surgical tool can be configured to restrict the amount of force and/or torque imparted on band 240 and/or to provide an indication to a medical practitioner of the amount of force and/or torque imparted on the band. In some embodiments, the amount of force and/or torque imparted on the band, and/or the amount of force and/or torque used to provide and indication to the medical practitioner, can be adjusted by the medical practitioner and/or can be determined by the configuration of the band selected for the procedure and/or by the physiology of the patient. As each gear 264 of gear rack 247 passes over the ratchet of fastening mechanism 250, the first portion 244 is prevented from retracting out of fastening mechanism 250. A portion of first portion 244 is removed from band 240. In some embodiments, a surgical tool can be used to remove the portion of the band 240 that extends beyond fastening mechanism 250. In such embodiments, the surgical tool can be configured to maintain a grip on the portion of the band 240 that extends beyond the fastening mechanism 250 and is to be removed. In this manner, the location of the removed portion of band 240 can be controlled prior to, and after, removal. Band 340 can be substantially similar to band 240 as shown in FIG. 10, and method 270 can be used to implant and deploy band 340.

Figure 12:
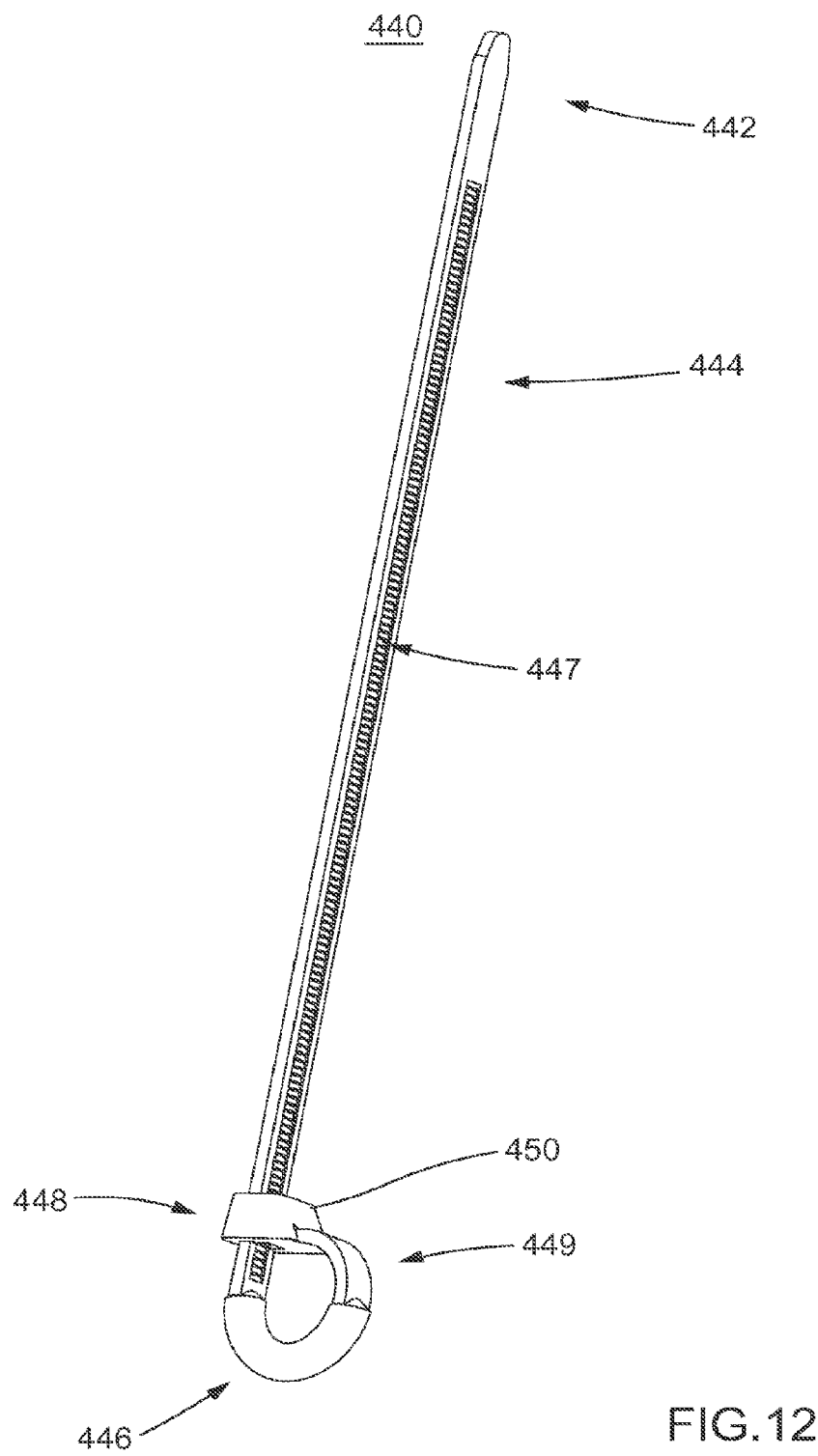
FIG. 12 is a perspective view of a flexible fastening band according to an embodiment.
Figure 13:
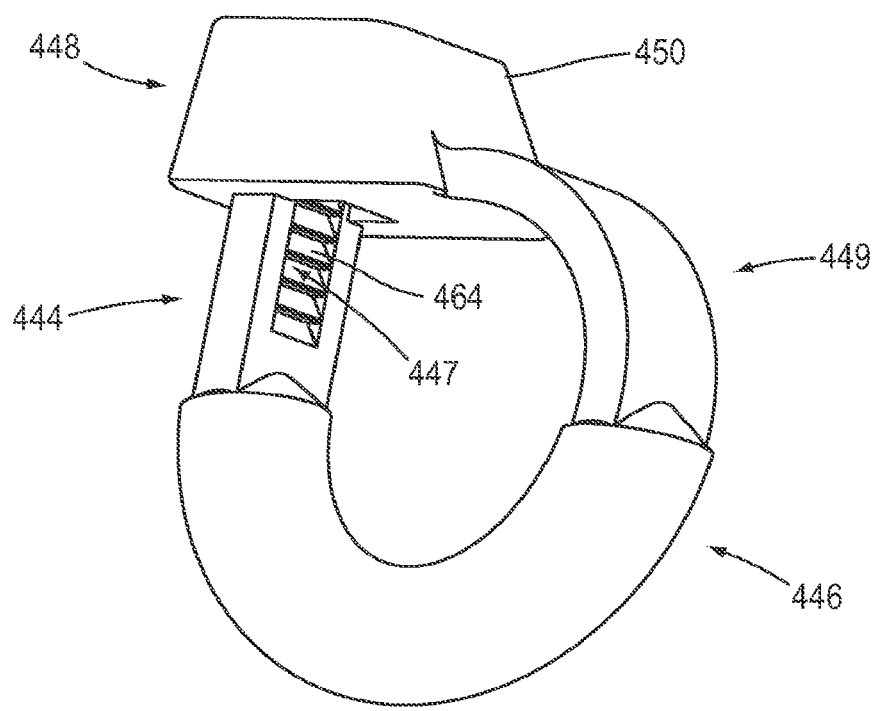
FIG. 13 is a perspective view of a portion of the flexible fastening band depicted in FIG. 12.
Figure 14:
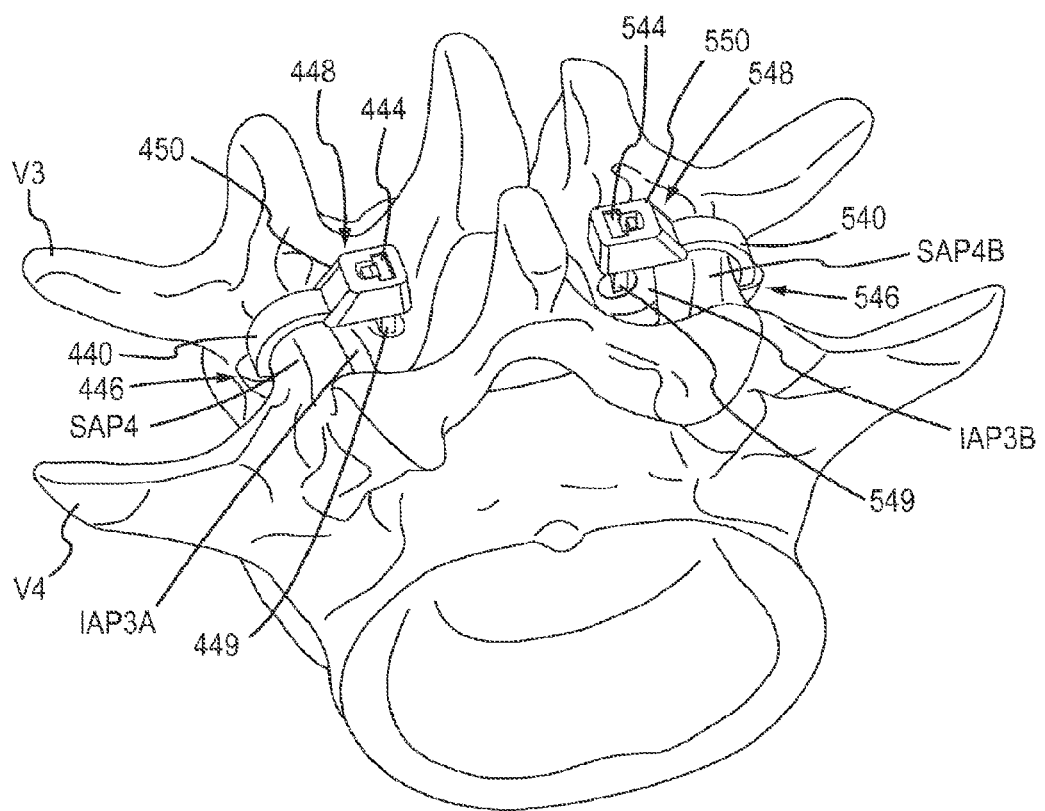
FIG. 14 is a posterior perspective view of a portion of the vertebral column depicting a stabilized vertebra including the flexible fastening band of FIG. 12 according to an embodiment.

FIG. 12 depicts views of a flexible fastening band ("band") 440, FIG. 13 depicts a view of a portion of band 440, and FIG. 14 shows a portion of the vertebral column with adjacent vertebrae stabilized using band 440 and a flexible fastening band ("band") 540 according to an embodiment. As shown in FIG. 14, a band 440 can be used to stabilize a vertebra V3 and vertebra V4 via the inferior articular process IAP3A of vertebra V3 and the superior articular process SAP4A of vertebra V4. Also as shown in FIG. 14, a band 540 is used to stabilize a vertebra V3 and vertebra V4 via the inferior articular process IAP3B of vertebra V3 and the superior articular process SAP4B of vertebra V4. In some embodiments, vertebra V3 and/or vertebra V3 are stabilized using only one of band 440 or band 540, as described above regarding band 240 and band 340.

Each of band 440 and band 540 can be similar to bands 140, 240, and 340 described above and can include similar components. By way of example, band 440 includes a proximal end portion 442, a first portion 444, a second portion 446, and a distal end portion 448 including a fastening mechanism 450, and band 540 includes a proximal end portion (not shown in FIG. 14), a first portion 544, a second portion 546, and a distal end portion 548 including a fastening mechanism 550. In contrast to band 240 and band 340, band 440 and band 540 each includes a cylindrical second portion 446, 546, and each includes a third portion 449, 549, respectfully. As depicted in FIGS. 12-14, third portion 449 is substantially the same shape as first portion 442, and as depicted in FIG. 14, third portion 549 is substantially the same shape as first portion 542. As can be seen in FIG. 14, second portion 446 is substantially the same diameter as the diameter of the lumen of superior articular process SAP4A of vertebra V4 and the diameter of the lumen of inferior articular process IAP3A of vertebra V3, and second portion 546 is substantially the same diameter as the diameter of the lumen of superior articular process SAP4B of vertebra V4 and the diameter of the lumen of inferior articular process IAP3B of vertebra V3. When the diameter of the second portion is substantially the same as the lumen of superior articular process SAP4B of vertebra V4 and the diameter of the lumen of inferior articular process IAP3B of vertebra V3, the amount of open space within the lumen can be minimized, the amount of surface area of the second portion of the band in contact with the lumen can increase, and subsequently the movement of vertebra V3 and/or vertebra V4 can be reduced or minimized. Furthermore, when movement of vertebra V3 and/or vertebra V4 does occur, forces acting against the band can be more equally distributed throughout the second portion of the band, due at least to the increased surface area of the band in contact with the lumen. As shown in FIGS. 12 and 13, band 440 includes a gear rack 447 and gears 464. Each of gears 464 can be wedge shaped to allow each of gears 464 to displace the ratchet of fastening mechanism 450 in only one direction. In some embodiments, gears 464 can be other shapes, such as blocks, etc.

Figure 15:
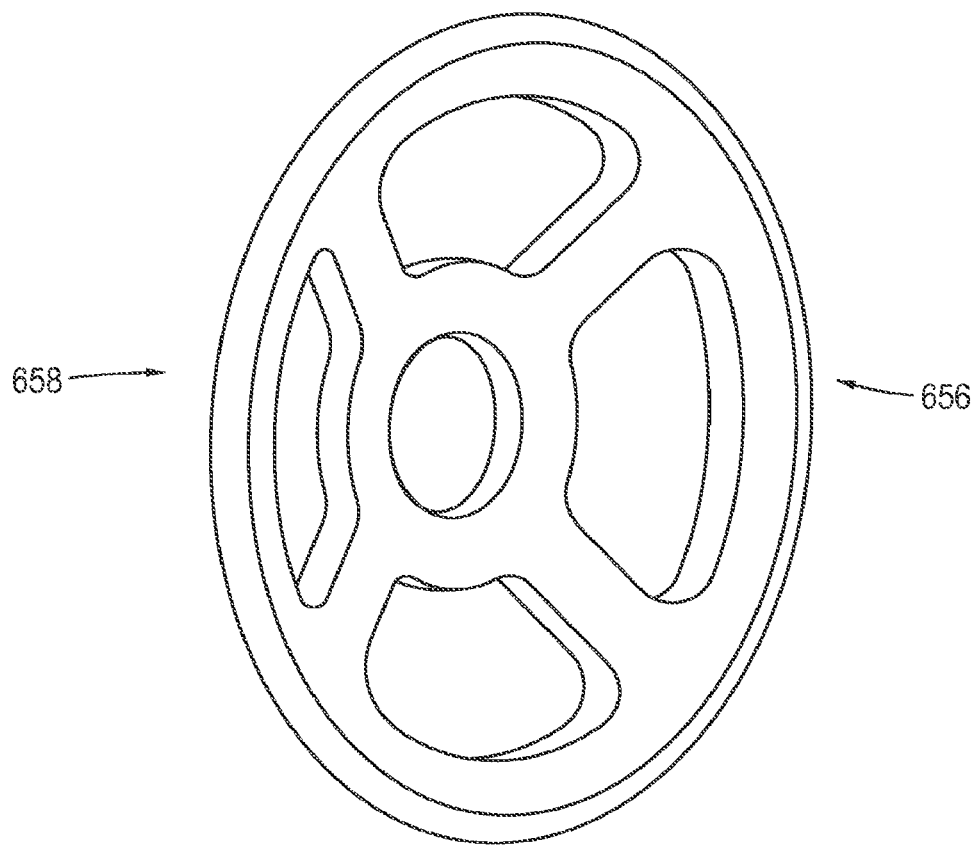
FIG. 15 is a perspective view of a spacer according to an embodiment.
Figure 16:
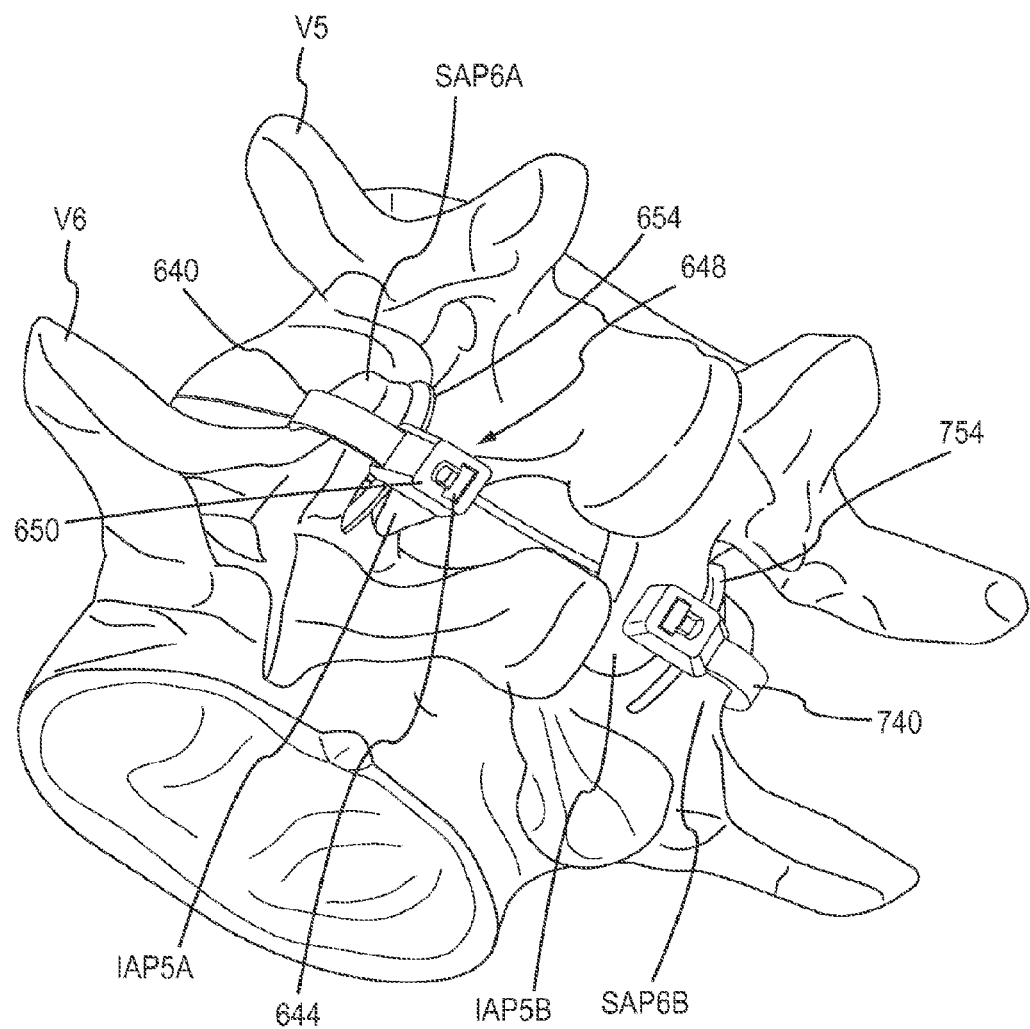
FIG. 16 is a posterior perspective view of a portion of the vertebral column depicting a stabilized vertebra including a flexible fastening band and the spacer of FIG. 15 according to an embodiment.

FIG. 15 depicts a perspective view of a spacer 654, and FIG. 16 depicts a portion of the vertebral column depicting a vertebra stabilized using a flexible fastening band ("band") 640 and spacer 654, and a flexible fastening band ("band") 740 and spacer 754 according to an embodiment. As shown in FIG. 16, a band 640 can be used to stabilize a vertebra V5 and vertebra V6 via the inferior articular process IAP5A of vertebra V5 and the superior articular process SAP6A of vertebra V5. Also as shown in FIG. 16, a band 740 is used to stabilize a vertebra V6 and vertebra V5 via the inferior articular process IAP5B of vertebra V5 and the superior articular process SAP6B of vertebra V6. In some embodiments, vertebra V5 and/or vertebra V6 are stabilized using only one of band 640 or band 740, as described above regarding band 240 and band 340.

Each of band 640 and band 740 can be similar to bands 140, 240, 340, 440, and 540 described above and can include similar components. In contrast to bands 140, 240, 340, 440, and 540, band 640 can include a spacer 654, and band 740 can include a spacer 754. While not shown, any of bands 140, 240, 340, 440, and 540, can include a spacer similar to spacer 654 and 754.

As shown in FIG. 15, spacer 654 can be substantially disc shaped. Spacer 654 can be can be similar to, and have similar features to the spacer described above and to the embodiments of the prosthesis shown and described in the '009 application. Spacer 654 can be implanted and deployed to restore the space between facets of a superior articular process of a first vertebra and an inferior articular process of an adjacent vertebra, can be implanted and deployed to help stabilize adjacent vertebrae with adhesives, and/or can be implanted and deployed to deliver a medication. In such embodiments, the spacer can be, for example, substantially disc shaped. In other embodiments, the spacer can be other shapes, e.g., square, elliptical, or any other shape. Spacer 654 include a first side 656 and a second side 658. As shown in FIG. 15, first side 656 is concave and second side 658 is convex. In some embodiments, first side 656 and/or the second side 658 can be convex, concave, or flat. Said another way, first side 656 of spacer 654 can be concave, convex, or flat, and second side 658 of spacer 654 can be concave, convex, or flat, e.g., first side 656 is concave and second side 658 is concave, first side 656 concave and second side 658 is convex, etc. In this manner, first side 656 and/or second side 658 can fit better against an articular process of a vertebra, specifically against a facet of the articular process of the vertebra. Spacer 654 can include, for example, the same materials as band 640. In some embodiments, spacer 654 can include substances configured to release medication and/or increase the stability of a vertebra and/or band 640. As discussed above, the substances can is include a medicine(s) and/or an adhesive(s).

Figure 17:
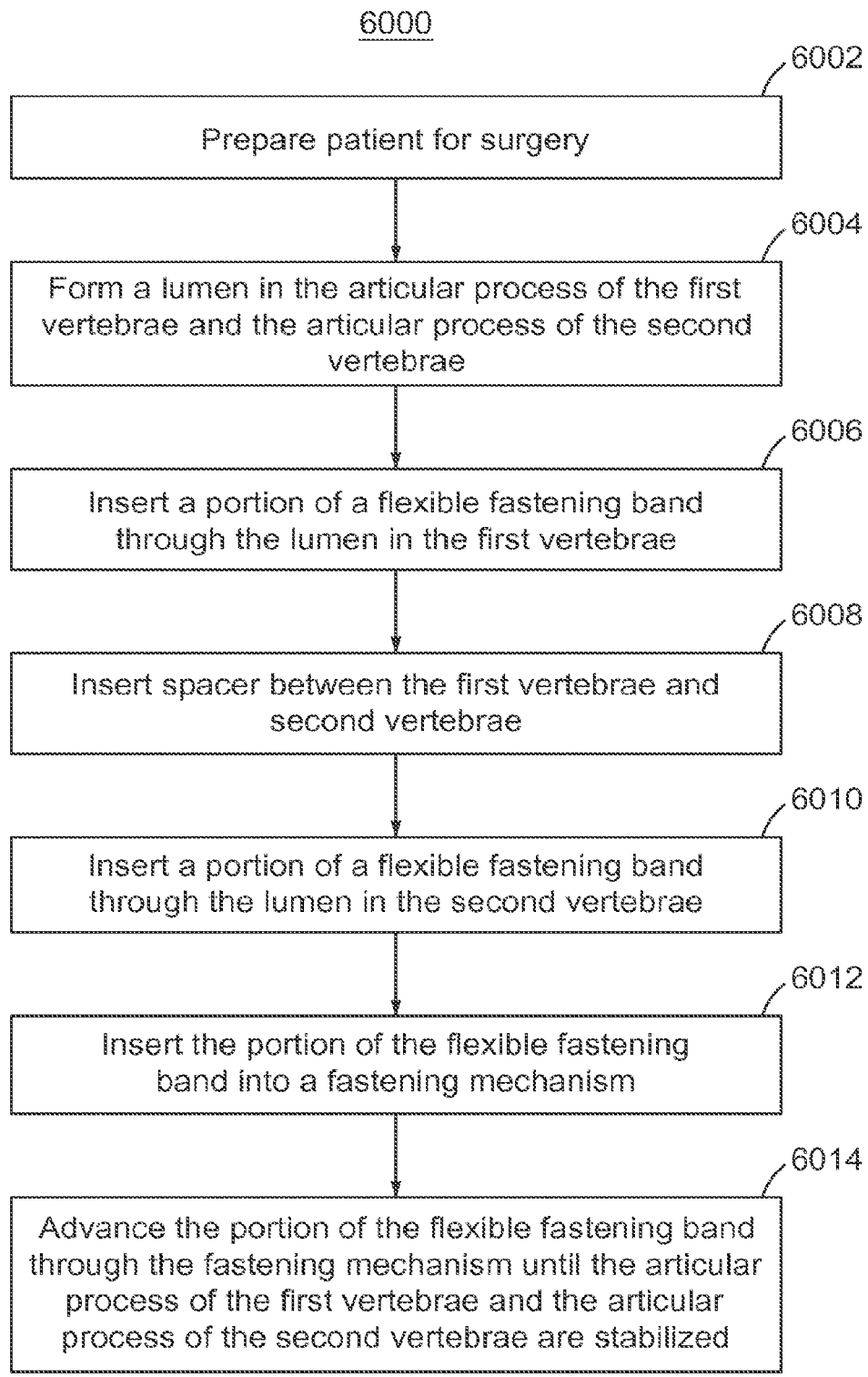
FIG. 17 is a flow chart illustrating a method of using a flexible fastening band and the spacer of FIG. 15.

FIG. 17 depicts a flow chart illustrating a method 6000 of using band 640 and/or band 740. Prior to use of band 640 and band 740, a patient can be prepared for surgery, at 6002. Some examples of preparations for surgery are described in the '009 application. In addition to those procedures described in the '009 application, in some embodiments, the surgical procedure can include direct visualization of the vertebra(e) to be stabilized. Said another way, the medical practitioner can perform the operation without the use of fluoroscopy, and, in this manner, may not have to rely on the inaccuracies and/or inconvenience inherent in fluoroscopic procedures. This direct visualization can be possible due to the small incision necessary for implantation of the band, for example, less than about 25 mm, and due to the ease of implanting and deploying the band. In some embodiments, the surgical procedure used can include forming an opening in body tissue substantially equidistant between a first articular process of the first vertebra and a second articular process of the first vertebra. A tube (not shown) can be inserted through the opening and a proximal end of the tube can be position near the lumen of superior articular process SAP6A of vertebra V6. A drill or other device can be used to form a lumen in superior articular process SAP6A of vertebra V6 and inferior articular process IAP5A of vertebra V5, at 6004. Specifically, the drill can be used to form the lumen in a facet of superior articular process SAP6A of vertebra V6 and to form the lumen in a facet of inferior articular process IAP5A of vertebra V5. Methods and devices for forming lumens in vertebra are described in the '009 application. The band 640 can be positioned within the tube and can be advanced through the tube until the proximal end portion is positioned near the lumen of superior articular process SAP6A of vertebra V6. In some embodiments, the proximal end of the tube can have a bend to direct the proximal end portion into the lumen of superior articular process SAP6A of vertebra V6. The proximal end portion is inserted into the lumen of superior articular process SAP6A of vertebra V6, at 6006. Spacer 654 is inserted between the superior articular process SAP6A of vertebra V6 and inferior articular process IAP5A of vertebra V5, at 6008. In some embodiments, spacer 654 can be disposed prior to inserting the proximal end portion into the lumen of superior articular process SAP6A of vertebra V6. The tube can be removed and/or reinserted at various points during the method 6000, including, for example, after the proximal end portion of band 640 is inserted into the lumen formed within the superior articular process SAP6A of vertebra V6, after vertebra V5 and/or Vertebra V6 has been stabilized, or at other points during method 6000. In some embodiments, first portion 644 can be advanced through the lumen of superior articular process SAP6A of vertebra V6 and through the lumen of inferior articular process IAP5A of vertebra V5 such that only the second portion is within the lumen of superior articular process SAP6A of vertebra V6 and through the lumen of inferior articular process IAP5A of vertebra V5. In this manner, when the shape of the second portion is substantially similar to the shape of the lumen of the superior articular process of the first vertebra and shape of the lumen of the inferior articular process of second vertebra, the lumen can only be contacted by that portion of the band, for example, the second portion, having the same shape.

The proximal end portion is inserted into the lumen of inferior articular process IAP5A of vertebra V5, at 6010. Proximal end portion 642 is inserted into the lumen of fastening mechanism 650 of distal end portion 648, at 6012. In some embodiments, to insert the proximal end portion into fastening mechanism 650 of distal end portion 648, a medical practitioner can grasp the proximal end portion and distal end 648, and manually insert the proximal end portion into fastening mechanism 650. In other embodiments, one or both of the proximal end portion and distal end portion 648 can be grasped with surgical tools (not shown). In such embodiments, the surgical tools can be configured to fit specific band configuration, for example, the surgical tools can be configured to receive distal end 648 without obstructing the lumen of fastening mechanism 650. By way of another example, the surgical tools can be configured to grasp and manipulate the proximal end portion and/or first portion 644. A portion of first portion 644 is advanced through the lumen of superior articular process SAP6A of vertebra V6 and through the lumen of inferior articular process IAP5A of vertebra V5. A portion of first portion 644 is advanced through the lumen of fastening mechanism 650 of distal end portion 648 until superior articular process SAP6A of vertebra V6 and inferior articular process IAP5A of vertebra V5 are stabilized, at 6014. In some embodiments, a surgical tool can be used to advance first portion 644 through the lumen of fastening mechanism 650. In such embodiments, one portion of the surgical tool can be configured to receive distal portion 648 without obstructing the lumen through fastening mechanism 650, one portion of the surgical tool can be configured to grip and/or advance the proximal end portion and or first portion 644. The surgical tool can be configured to restrict the amount of force and/or torque imparted on band 640 and/or to provide an indication to a medical practitioner of the amount of force and/or torque imparted on the band. In some embodiments, the amount of force and/or torque imparted on the band, and/or the amount of force and/or torque required to provide and indication to the medical practitioner, can be adjusted by the medical practitioner and/or can be determined by the configuration of the band selected for the procedure and/or by the physiology of the patient. As each gear of the gear rack passes over the ratchet of the fastening mechanism, the first portion 644 is prevented from retracting out of the fastening mechanism. A portion of first portion 644 is removed from band 640. In some embodiments, a surgical tool can be used to remove the portion of the band 640 that extends beyond fastening mechanism 650. In such embodiments, the surgical tool can be configured to maintain a grip on the portion of the band 640 that extends beyond fastening mechanism 250 and is to be removed. In this manner, the location of the removed portion of band 640 can be controlled prior to, and after, removal. Band 740 and spacer 754 can be substantially similar to band 640 and spacer 654, and method 770 can be used to implant and deploy band 740 and spacer 754.

Figure 18:
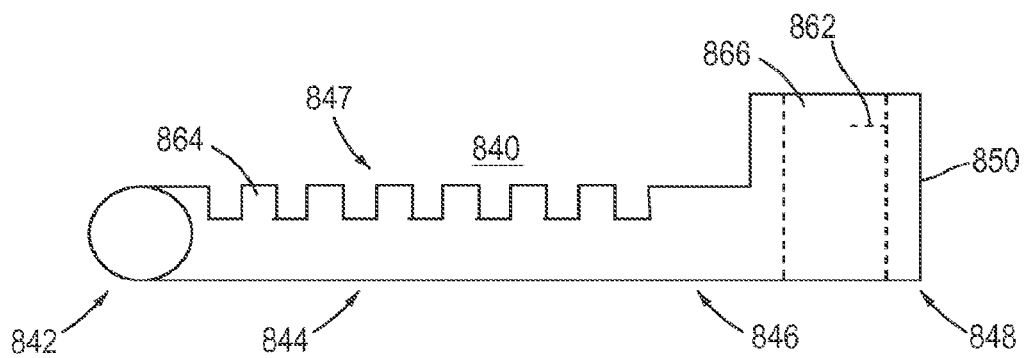
FIG. 18 is a side view of a flexible fastening band according to an embodiment.
Figure 19:
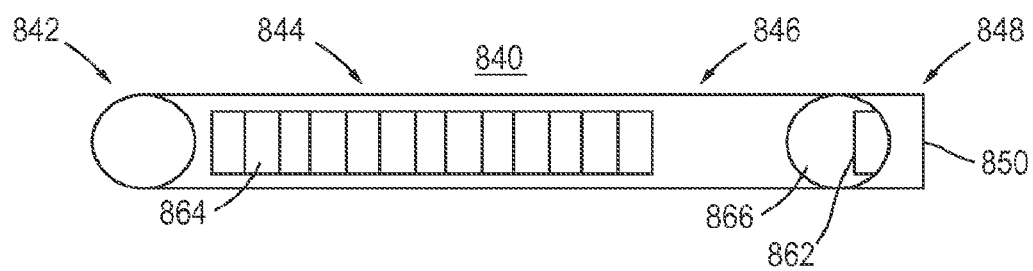
FIG. 19 is a top view the flexible fastening band depicted in FIG. 18.

FIG. 18 is a side view and FIG. 19 is a top view of a flexible fastening band ("band") 840 according to another embodiment. Band 840 can be similar to band 140 and band 240 described above and can include similar components. By way of example, band 840 includes a proximal end portion 842, a first portion 844 including a gear rack 847, a second portion 846, and a distal end portion 848 including a fastening mechanism 850 and a ratchet 862. In contrast to gear rack 247, a cross sectional area of each gear 864 of gear rack 847 is rectangular in shape instead of wedge shaped. Furthermore, in contrast to first portion 244, first portion 844 is cylindrical in shape instead of cuboidal in shape. In this manner, the lumen 866 of the fastening mechanism 850 is cylindrical in shape. A band according to this embodiment may be particularly useful in deployments where a single band in used to stabilize adjacent vertebrae. In this manner, the second portion can be disposed within the lumen of the first articular process of the first vertebra and a portion of the first portion can be disposed within the lumen of the second articular process of the first vertebra. In these embodiments the portion of the band within the first articular process of the first vertebra and the portion of the band within in the second articular process of the first vertebra can both have substantially the same shape as the lumen in the first articular process of the first vertebra and the lumen in the second articular process of the first vertebra. In this manner, and as described above regarding band 440, the amount of open space within the lumens can be minimized, the amount of surface area of the first portion and/or second portion of the band in contact with the lumens can increase, and subsequently the movement of the first vertebra and/or the second vertebra can be reduced or minimized. Furthermore, when movement of the first vertebra and/or the second vertebra does occur, forces acting against the band can be more equally distributed throughout the first portion and/or the second portion, due at least to the increased surface area of the band in contact with the lumens.

Figure 20:
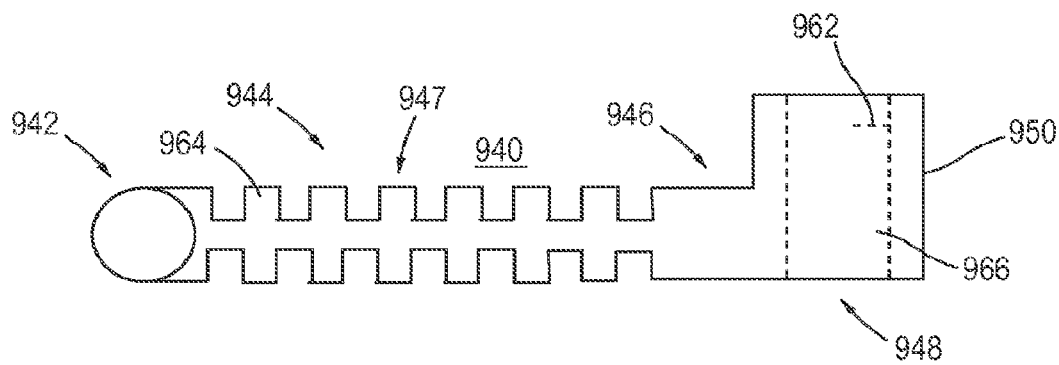
FIG. 20 is a side view of a flexible fastening band according to an embodiment.

FIG. 20 is a side view a flexible fastening band ("band") 940 according to an embodiment. Band 940 can be similar to band 140, band 240, and band 840 described above and can include similar components. By way of example, band 940 includes a proximal end portion 942, a first portion 944 including a gear rack 947, a second portion 946, and a distal end portion 948 including a fastening mechanism 950. Similar to gear rack 847, a cross sectional area of each gear 964 of gear rack 947 is rectangular in shape. In contrast to gear rack 847, each of gears 964 extend the entire circumference of first portion 944 instead of only a portion of the circumference of first portion 844. Furthermore, in contrast to first portion 244, but similar to first portion 844, first portion 944 is cylindrical in shape instead of cuboidal in shape. In this manner, the lumen 966 of the fastening mechanism 950 is cylindrical in shape. A band according to this embodiment may be particularly useful in deployments where the movement and repositioning of the band after implantation may be difficult. In this manner, because each of the gears can be the entire circumference of the first portion and/or the second portion, the first portion and/or the second portion can enter the fastening mechanism in any radial orientation and still engage the ratchet.

Figure 21:
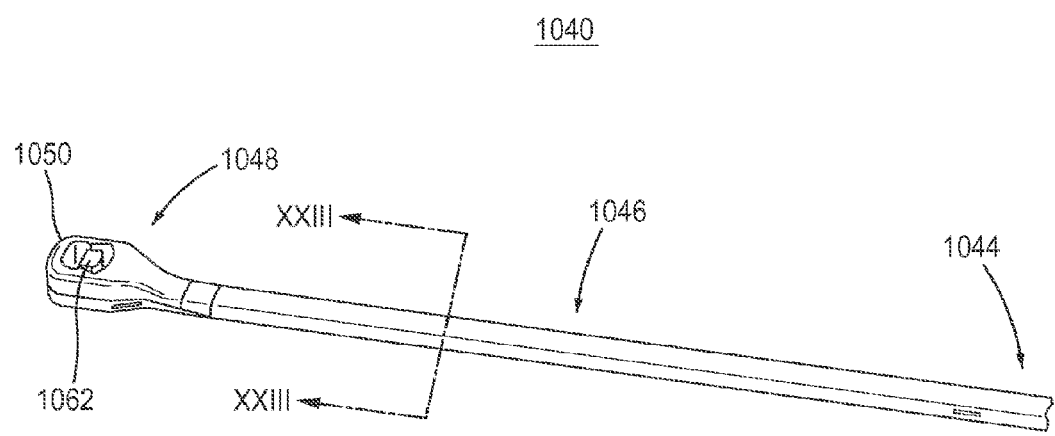
FIG. 21 is a perspective view of a flexible fastening band according to an embodiment.
Figure 22:
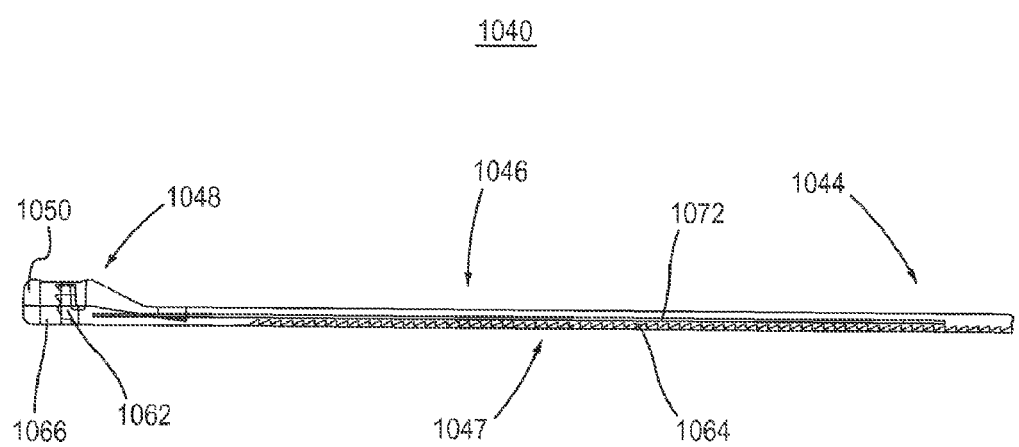
FIG. 22 is a cross-sectional side view of the flexible fastening band depicted in FIG. 21.
Figure 23:
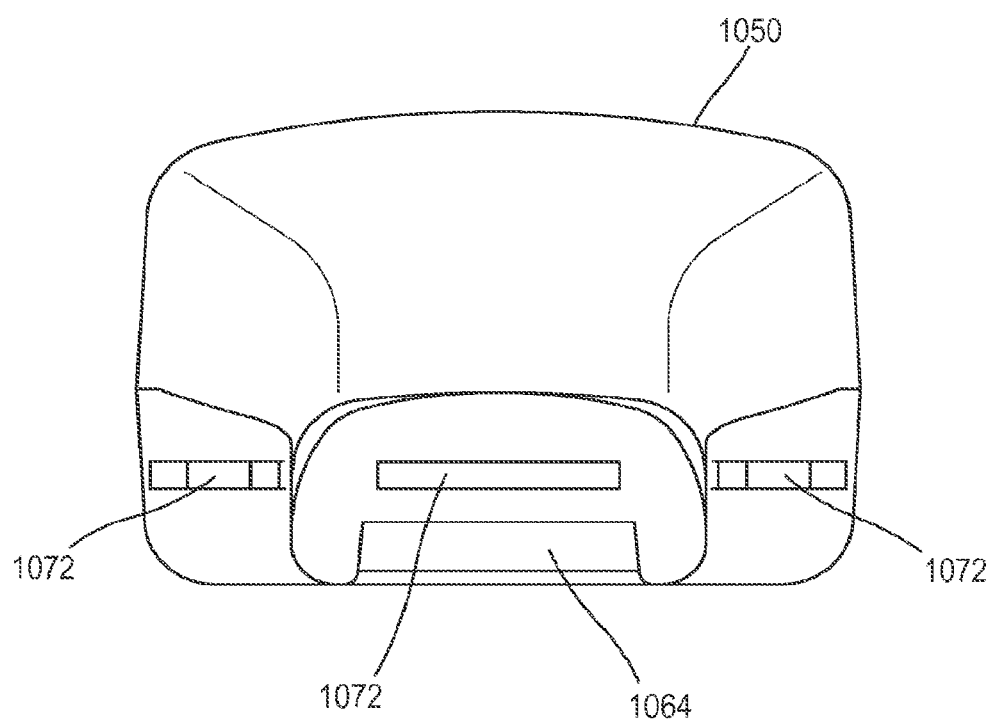
FIG. 23 is a cross-sectional view taken along line XXIII of the flexible fastening band depicted in FIG. 21.
Figure 24:
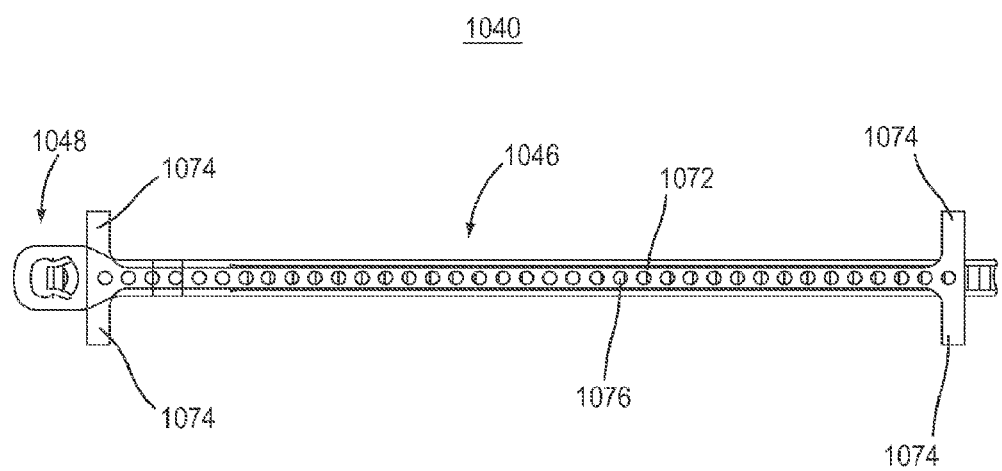
FIG. 24 is a cross-sectional top view of the flexible fastening band depicted in FIG. 21 in a first configuration.
Figure 25:
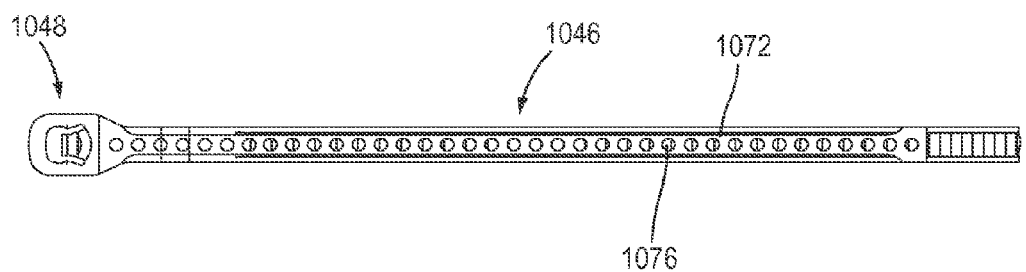
FIG. 25 is a cross-sectional top view of the flexible fastening band depicted in FIG. 21 in a second configuration.

FIGS. 21-25 are views of a flexible fastening band ("band") 1040 according to another embodiment. FIG. 21 is a perspective view and FIG. 22 is a cross-sectional side view of band 1040. FIG. 23 is a cross-sectional view of band 1040 taken along line XXIII. FIG. 24 is a cross-sectional top view of band 1040 in a first configuration and FIG. 25 is a cross-sectional top view of band 1040 in a second configuration. Band 1040 can be similar to band 140 and band 240 described above and can include similar components. By way of example, band 1040 includes a proximal end portion (not shown), a first portion 1044 including a gear rack 1047 (see FIG. 22), a second portion 106, and a distal end portion 1048 including a fastening mechanism 1050 and a ratchet

1062. In contrast to band 140 and band 240, band 1040 includes a reinforcement piece 1072.

Reinforcement piece 1072 can include any of the materials described above for band 140. In some embodiments, reinforcement piece 1072 can include a material stronger than second portion 1046 and/or first portion 1044, for example, first portion 1044 and second portion 1046 can include PEEK and reinforcement piece 1072 can include titanium. As shown in FIG. 22, reinforcement piece 1072 can be disposed within band 1040 approximately along the entire length of second portion 1046, and a portion of reinforcement piece 1072 can be disposed within the distal end portion 1048. In some embodiments, reinforcement piece can include a length along at least a portion of the length of second portion 1046 and/or first portion 1044 but not the distal end portion. In some embodiments, reinforcement piece 1072 can be disposed only within second portion 1046. Reinforcement piece 1072 can have a length in first dimension (length), a length in a second dimension (width), and a length in a third dimension (height). As described herein, a reinforcement piece be different shapes that can include more or fewer dimensions.

The reinforcement piece can be molded within the band. Said another way, in embodiments where the first portion, the second portion, and or the distal end portion are moldable materials, the reinforcement piece can be placed in the mold and the moldable materials can be injected or otherwise put in the mold around the reinforcement piece. In other embodiments, each portion of the band (for example, the proximal end portion, the first portion, the second portion, the third portion, and/or the distal end portion) around the reinforcement piece can have a top half and a bottom half, and each of the top half and the bottom half can be placed around the reinforcement piece, and sealed. As shown in FIG. 24, reinforcement piece 1072 includes support members 1074. While FIG. 24 shows reinforcement piece 1072 including four support members 1074, in some embodiments, more or fewer support members 1074 can be used. Support members 1074 can maintain the position of reinforcement piece 1072 during the molding and/or assembly process of band 1040. As shown in FIG. 25, support members 1074 are removed before band 1040 is used.

As shown in FIG. 23, reinforcement piece 1072 can has a substantially uniform cuboidal shape. In other embodiments, reinforcement piece 1072 can have other shapes. The shape of the reinforcement piece can be selected depending on the desired bending and/or torsion characteristics of the material chosen. By way of example, a substantially planar cuboidal shape can provide a greater increase in bending strength while providing a lesser increase in torsion strength, a cylindrical shape can provide an increase in bending strength while providing very little increase in torsion strength, a substantially square and/or tubular cuboidal shape can provide similar bending and torsion increases. Any shape can be selected to achieve the desired bending and torsion strength. Combinations of materials and shapes can also be considered. For example, a material having higher torsion strength may be combined with a shape having a lower torsion strength to combine for the desired torsion strength. As shown in FIGS. 24 and 25, reinforcement piece 1072 includes holes 1076 distributed along the length of the first dimension. While FIGS. 24 and 25 shows band 1040 including many holes 1076, in some embodiments, more or fewer holes 1076 can be used. FIGS. 24 and 25 depict holes 1076 distributed substantially equally along the length of the first dimension, in some embodiments, the holes can be distributed differently or along different dimensions depending on the shape and/or material chosen, and/or whether the reinforcement piece is solid or hollow. Holes 1076 can be configured to reduce the weight of reinforcement piece 1072 while still provided band 1040 additional strength. Holes 1076 can be round, oval, square, or any other shape.

Figure 26:
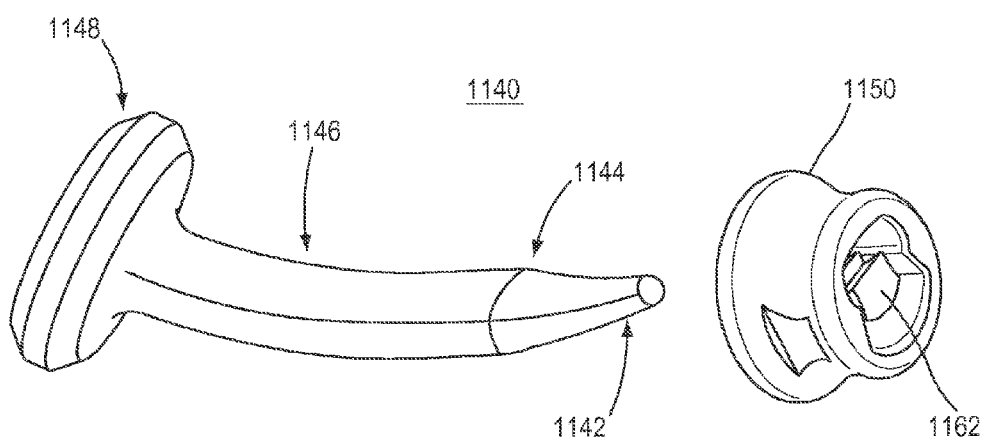
FIG. 26 is an exploded view of a flexible fastening band according to an embodiment.
Figure 27:
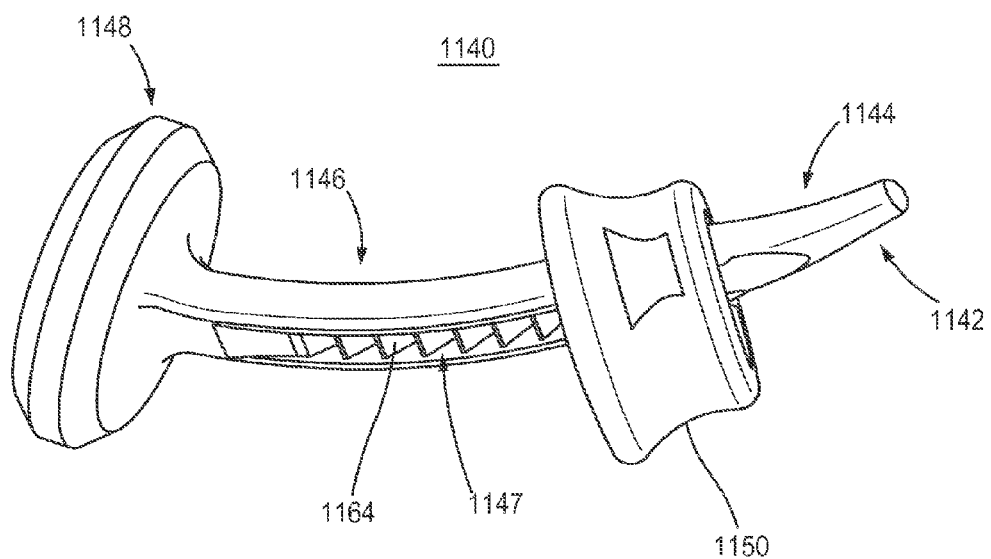
FIG. 27 is a perspective view of the flexible fastening band depicted in FIG. 26.
Figure 28:
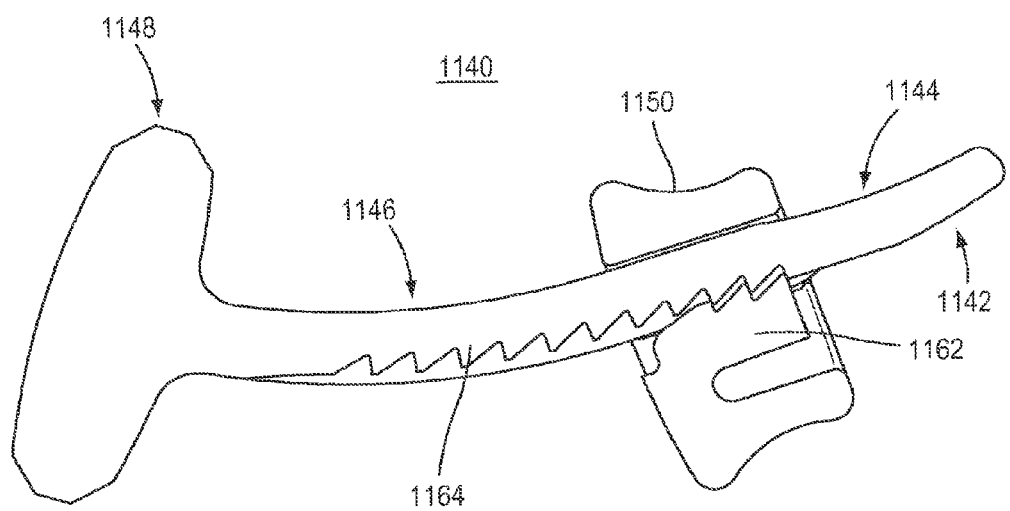
FIG. 28 is a cross-sectional view of the flexible fastening band depicted in FIG. 27.

FIG. 26 is an exploded view, FIG. 27 is a perspective view, and FIG. 28 is a cross-sectional view of a flexible fastening band ("band") 1140 according to another embodiment. Band 1140 can be similar to band 140 and band 240 described above and can include similar components. By way of example, band 1140 includes a proximal end portion 1142, a first portion 1144, a second portion 1146 including a gear rack 1147, a distal end portion 1148, a fastening mechanism 1150 and a ratchet 1162. In contrast to band 140 and band 240, the fastening mechanism 1150 of band 1140 is separately formed from band 1140. While second portion 1146 of band 1140 is shown in FIGS. 26-28 as having a substantially cuboidal shape, in some embodiments, second portion 1146 can be substantially cylindrical in shape or any other appropriate shape discussed herein. As shown in FIGS. 27 and 28, band 1140 includes a gear rack 1147 and gears 1164. Each of gears 1164 can be wedge shaped to allow each of gears 1164 to displace a ratchet 1162 of fastening mechanism 1150 in only one direction. In some embodiments, gears 1164 can be other shapes, such as blocks, or any other appropriate shape discussed herein. As shown in FIGS. 26-28, distal end portion 1148 can be substantially circular in shape and can have a diameter greater than a width of second portion 1146. In other embodiments, distal portion 1148 can have other shapes, for example, oval, rectangular, square, etc.

Figure 29:
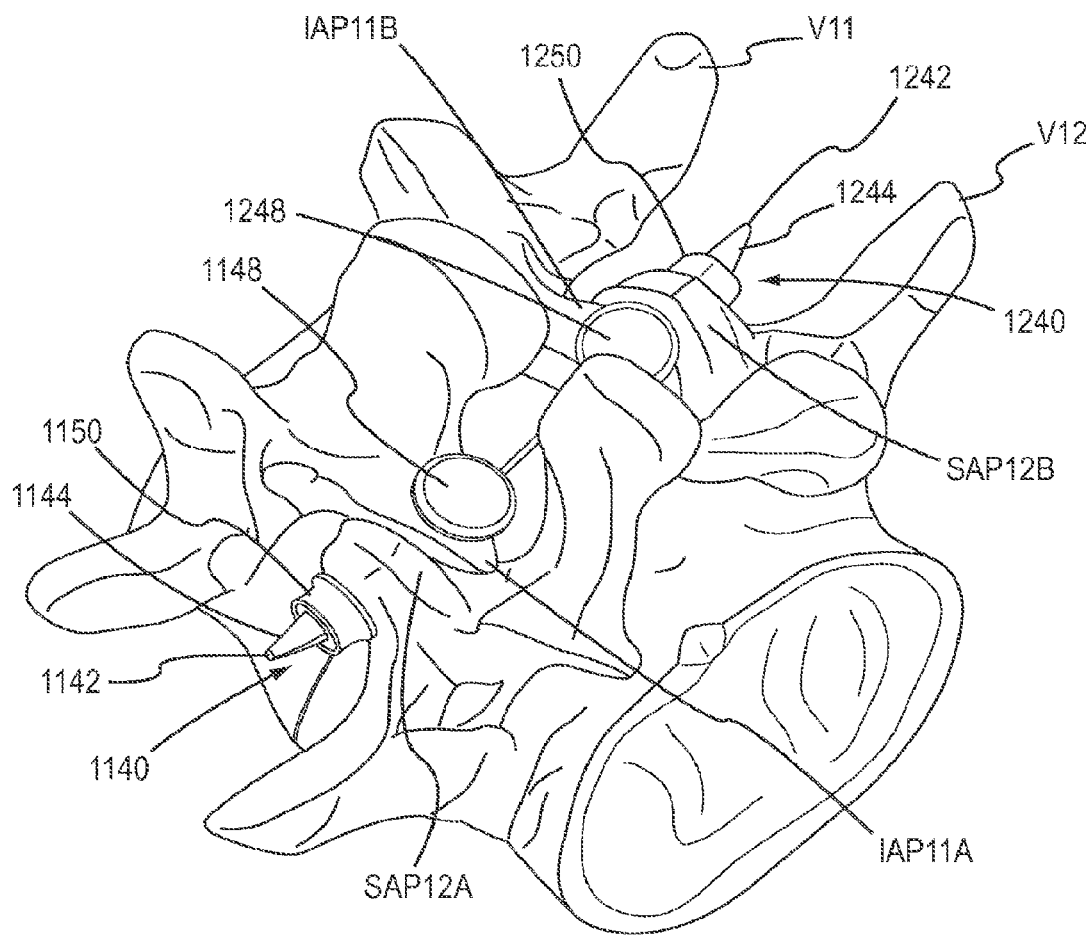
FIG. 29 is a posterior perspective view of a portion of the vertebral column depicting a stabilized vertebra including two flexible fastening bands of FIG. 26.

FIG. 29 shows a posterior perspective view of a portion of the vertebral column during a method for stabilizing adjacent vertebrae using band 1140 and a flexible fastening band ("band") 1240 according to an embodiment. Band 1240 can be similar to band 1140 described above and can include similar components. By way of example, band 1240 includes a proximal end portion 1242, a first portion 1244, a second portion 1246, a distal end portion 1248, and a fastening mechanism 1250.

As shown in FIG. 29, a band 1140 can be used to stabilize a vertebra V11 and a vertebra V12 via the inferior articular process IAP11A of vertebra V11 and the superior articular process SAP12A of vertebra V12. Also as shown in FIG. 29, band 1240 is used to stabilize a vertebra V11 and vertebra V12 via the inferior articular process IAP11B of vertebra V11 and the superior articular process SAP12B of vertebra V12. In some embodiments, vertebra V11 and/or vertebra V12 are stabilized using only one of band 1140 or band 1240. In some such embodiments, one of band 1140 or band 1240 can be used to stabilize vertebra V11 and/or vertebra V12 via one of via the inferior articular process IAP11A of vertebra V11 and the superior articular process SAP12A of vertebra V12, or, via the inferior articular process IAP11B of vertebra V11 and the superior articular process SAP12B of vertebra V12.

Either of band 1140 and/or band 1240 can be used in accordance with any of the methods described herein. By way of example, second portion 1146 of band 1140 can be disposed in a lumen of IAP11A of vertebra V11 and in a lumen of SAP12A of vertebra V12. Proximal end portion 1142 is inserted into a lumen of fastening mechanism 1150. In some embodiments, to insert proximal end portion 1142 into fastening mechanism 1150, a medical practitioner can grasp proximal end portion 1142 and fastening mechanism 1150, and manually insert proximal end portion 1142 into fastening mechanism 1150. In other embodiments, one or both of proximal end portion 1142 and fastening mechanism 1150 can be grasped with surgical tools (not shown). In such embodiments, the surgical tools can be configured to fit specific band configuration, for example, the surgical tools can be configured to receive fastening mechanism 1150 without obstructing the lumen of fastening mechanism 1150. A portion of first portion 1144 is advanced through the lumen of fastening mechanism 1150 until superior articular process SAP12A of vertebra V12 and inferior articular process IAP11A of vertebra V11 are stabilized.

Figure 30:
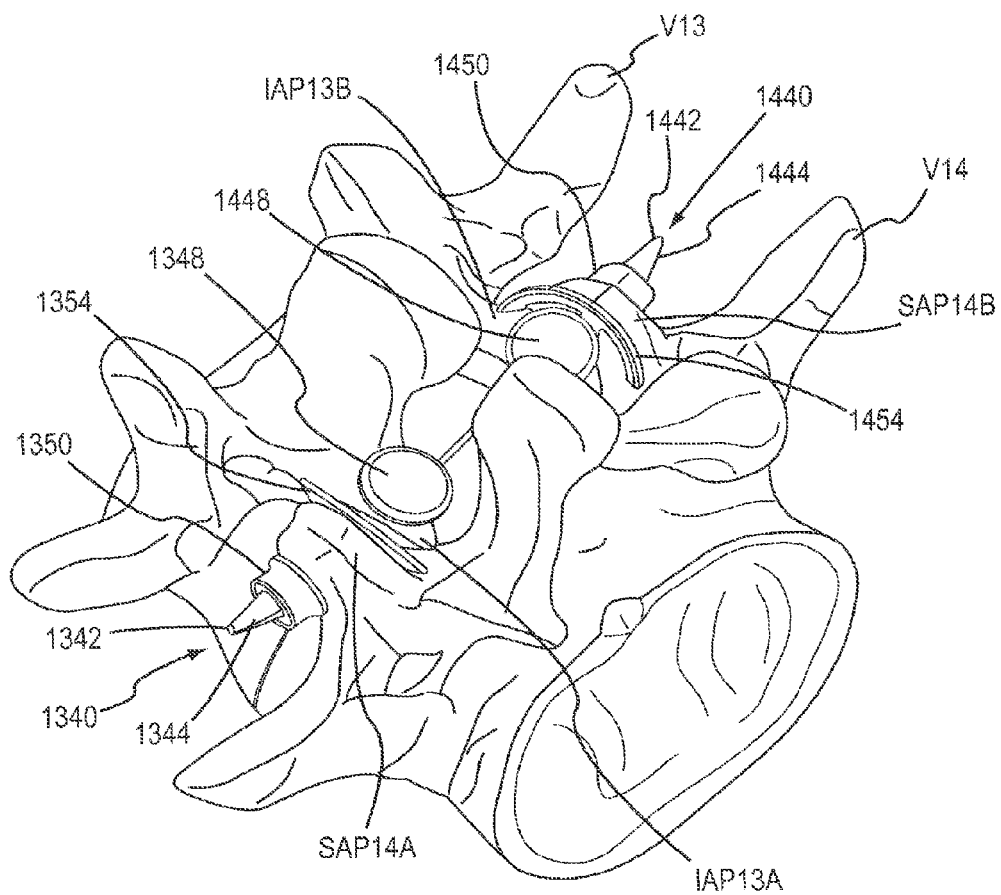
FIG. 30 is a posterior perspective view of a portion of the vertebral column depicting a stabilized vertebra including two flexible fastening bands and two spacers according to an embodiment

FIG. 30 shows a posterior perspective view of a portion of the vertebral column during a method for stabilizing adjacent vertebrae using a flexible fastening band ("band") 1340 and a flexible fastening band ("band") 1440 according to an embodiment. Each of band 1340 and band 1440 can be similar to band 1140 described above and can include similar components. By way of example, band 1340 includes a proximal end portion 1342, a first portion 1344, a second portion (not shown in FIG. 30), a distal end portion 1348, and a fastening mechanism 1350; band 1440 includes a proximal end portion 1442, a first portion 1444, a second portion (not shown in FIG. 30), a distal end portion 1448, and a fastening mechanism 1450. In contrast to band 1140 and band 1240, band 1340 includes a spacer 1354, and band 1440 includes a spacer 1454. Each of spacer 1354 and spacer 1454 can be similar to can be similar to spacer 654 described above and can include similar components.

As shown in FIG. 30, a band 1340 can be used to stabilize a vertebra V13 and a vertebra V14 via the inferior articular process IAP13A of vertebra V13 and the superior articular process SAP14A of vertebra V14. Also as shown in FIG. 30, band 1440 is used to stabilize a vertebra V13 and vertebra V14 via the inferior articular process IAP13B of vertebra V13 and the superior articular process SAP14B of vertebra V14. In some embodiments, vertebra V13 and/or vertebra V14 are stabilized using only one of band 1340 or band 1440. In some such embodiments, one of band 1340 or band 1440 can be used to stabilize vertebra V13 and/or vertebra V14 via one of via the inferior articular process IAP13A of vertebra V13 and the superior articular process SAP14A of vertebra V14, or, via the inferior articular process IAP13B of vertebra V13 and the superior articular process SAP14B of vertebra V14.

Either of band 1340 and/or band 1440 can be used in accordance with any of the methods described herein. By way of example, the second portion of band 1340 can be disposed in a lumen of IAP13A of vertebra V13, spacer 1354 can be disposed between IAP13A and SAP14A, and the second portion of band 1340 can be disposed in a lumen of SAP14A of vertebra V14. Proximal end portion 1342 is inserted into a lumen of fastening mechanism 1350. In some embodiments, to insert proximal end portion 1342 into fastening mechanism 1350, a medical practitioner can grasp proximal end portion 1342 and fastening mechanism 1350, and manually insert proximal end portion 1342 into fastening mechanism 1350. In other embodiments, one or both of proximal end portion 1342 and fastening mechanism 1350 can be grasped with surgical tools (not shown). In such embodiments, the surgical tools can be configured to fit specific band configuration, for example, the surgical tools can be configured to receive fastening mechanism 1350 without obstructing the lumen of fastening mechanism 1350. A portion of first portion 1344 is advanced through the lumen of fastening mechanism 1350 until superior articular process SAP14A of vertebra V14 and inferior articular process IAP13A of vertebra V13 are stabilized.

While various embodiments have been described above, it should be understood that they have been presented by way of example only, not limitation, and various changes in form and details may be made. For example, while the descriptions given are with reference to stabilizing vertebra, another bone(s), such as, for example, a sternum and/or a rib(s) could be stabilized using the flexible fastening bands described herein. In another example, a flexible fastening band can be used to stabilize and/or fixate an intramedullary (IM) rod or nail. For example, the flexible fastening band can be used at different longitudinal locations along an IM rod or nail, and used to couple adjacent bone portions to the IM rod or nail. In such situations, a given flexible fastening band can fix a first bone portion, the IM rod or nail, and a second bone portion, all of which are positioned between the distal portion and the proximal portion of the flexible fastening band. In yet another example, a flexible fastening band can be used to stabilize and/or fixate a bone fragment. While various embodiments have been described above with regard to natural bone spaces, (e.g., the space between an inferior articulate process and a superior articulate process), in other embodiments, the bone spacing can be man-made (e.g., sternum split during a heart procedure), and/or due to an injury (e.g., broken bone).

Where methods described above indicate certain events occurring in certain order, the ordering of certain events can be modified. Additionally, certain of the events can be performed concurrently in a parallel process when possible, as well as performed sequentially as described above. Any portion of the apparatus and/or methods described herein may be combined in any combination, except mutually exclusive combinations. The embodiments described herein can include various combinations and/or sub-combinations of the functions, components and/or features of the different embodiments described. For example, FIGS. 18 and 19 depict band 840 including a single ratchet 862, and FIG. 20 depicts band 940 including a single ratchet 962, however, in some embodiments, any of bands 140-1440 can include any number of ratchets. Similarly, any of bands 140-1440 can include a reinforcement piece and/or a spacer.

What is claimed is:

1. An apparatus, comprising:
   a flexible elongate body including a proximal end portion, a first portion, a second portion, and a distal end portion;
   the distal end portion of the flexible elongate body including a fastener configured to accept the proximal end portion and the first portion;
   wherein the first portion and the second portion have substantially the same cross-sectional shape and comprise a first material; and
   wherein the first portion is more flexible than the second portion.

2. The apparatus of claim 1, wherein the fastener defines a lumen.

3. The apparatus of claim 1, wherein the flexible elongate body has different torsion characteristics along a length of the flexible elongate body.

4. The apparatus of claim 1, wherein the first material is PEEK.

5. The apparatus of claim 1, wherein the entire flexible elongate body is made of the first material.

6. The apparatus of claim 1, further comprising a reinforcement portion comprising a second material, stronger than the first material, the reinforcement portion being disposed within at least a portion of the second portion.

7. The apparatus of claim 6, wherein the reinforcement portion defines a plurality of holes distributed along a first dimension, the reinforcement portion having a length in the first dimension greater than a length in a second dimension or a length in a third dimension.

8. The apparatus of claim 6, wherein the reinforcement portion is disposed within a portion of the distal end portion.

9. An apparatus, comprising:
a flexible elongate body including a proximal end portion, a first portion, a second portion distal to the first portion, and a distal end portion; and
a fastener configured to accept the proximal end portion and the first portion;
the first portion of the flexible elongate body having a length and a substantially uniform cross-sectional first shape, the first portion having a recessed engagement portion;
the second portion of the flexible elongate body having a length and a substantially uniform cross-sectional second shape, different from the first cross-sectional shape, that is configured to substantially compliment a shape of first bone portion and a shape of a second bone portion; and
the fastener configured to receive the recessed engagement portion of the first portion of the flexible elongate body when the second portion of the flexible elongate body is disposed in contact with the first bone portion and in contact with the second bone portion.

10. The apparatus of claim 9, wherein the fastener is configured to allow the first portion of the flexible elongate body to travel through the fastener in only one direction.

11. The apparatus of claim 9, wherein the flexible elongate body and the fastener are monolithically formed.

12. The apparatus of claim 9, wherein the length of the first portion of the flexible elongate body is more than twice as long as the length of the second portion of the flexible elongate body.

13. The apparatus of claim 9, wherein the first shape is substantially cuboidal and the second shape is substantially cylindrical.

14. The apparatus of claim 9, wherein the cross-sectional area of the second portion of the flexible elongate body is greater than the cross-sectional area of the first portion of the flexible elongate body.

15. The apparatus of claim 9, wherein the second portion of the flexible elongate body is separately formed from the first portion of the flexible elongate body.

16. The apparatus of claims 9, wherein the second portion of the flexible elongate body defines a lumen having the first shape, the first portion of the flexible elongate body is configured to be slideably disposed in the lumen of the second portion of the flexible elongate body.

17. The apparatus of claim 9, wherein the fastener defines a lumen having a cross-sectional area less than the cross-sectional area of the second portion of the flexible elongate body.

18. The apparatus of claim 9, further including a spacer disposed about the second portion of the flexible elongate body.

19. The apparatus of claim 18, wherein the spacer is configured to release one of an adhesive or a medicine.

20. The apparatus of claim 9, wherein the fastener is separately formed from the flexible elongate body.

21. An apparatus, comprising:
a flexible elongate body including a proximal end portion, a first portion, a second portion mutually exclusive from and distal to the first portion, and a distal end portion; and
a fastener configured to accept the proximal end portion and the first portion;
the first portion of the flexible elongate body having a length and a substantially uniform first shape, the first portion having a recessed engagement portion;
the second portion of the flexible elongate body having a length and a substantially uniform second shape, different from the first shape, that is configured to substantially compliment a shape of first bone portion and a shape of a second bone portion; and
a third portion, disposed between the second portion and the distal end portion, and having the first shape;
the fastener configured to receive the recessed engagement portion of the first portion of the flexible elongate body when the second portion of the flexible elongate body is disposed in contact with the first bone portion and in contact with the second bone portion.

* * * * *